(12) United States Patent
Pedersen et al.

(10) Patent No.: US 11,759,574 B2
(45) Date of Patent: Sep. 19, 2023

(54) ACCESSORY DEVICE WITH MOUNTING FEATURE FOR ENGAGING DIAL MEMBER

(71) Applicant: Novo Nordisk A/S, Bagsvaerd (DK)

(72) Inventors: Bennie Peder Smiszek Pedersen, Haslev (DK); Laurits Hoejgaard Olesen, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 450 days.

(21) Appl. No.: 16/969,207

(22) PCT Filed: Feb. 18, 2019

(86) PCT No.: PCT/EP2019/053982
§ 371 (c)(1),
(2) Date: Aug. 12, 2020

(87) PCT Pub. No.: WO2019/162235
PCT Pub. Date: Aug. 29, 2019

(65) Prior Publication Data
US 2020/0405968 A1 Dec. 31, 2020

(30) Foreign Application Priority Data
Feb. 20, 2018 (EP) .................................... 18157609

(51) Int. Cl.
*A61M 5/315* (2006.01)
*A61M 5/20* (2006.01)
*A61M 5/24* (2006.01)
*A61M 5/31* (2006.01)

(52) U.S. Cl.
CPC ....... *A61M 5/31551* (2013.01); *A61M 5/2033* (2013.01); *A61M 5/2466* (2013.01);
(Continued)

(58) Field of Classification Search
CPC ............ A61M 5/31551; A61M 5/2033; A61M 5/2466; A61M 2005/3126; A61M 2205/3317; A61M 2205/52
See application file for complete search history.

(56) References Cited

U.S. PATENT DOCUMENTS 10,105,497 B2   10/2018  Dreier et al.
10,286,156 B2    5/2019  Groeschke et al.
(Continued)

FOREIGN PATENT DOCUMENTS

CN   105073165 A   11/2015
CN   105120924 A   12/2015
(Continued)

*Primary Examiner* — Dung T Ulsh
(74) *Attorney, Agent, or Firm* — Wesley Nicolas

(57) ABSTRACT

An assembly comprising a drug delivery device and an add-on device adapted to be releasably mounted thereon, the drug delivery device comprising a rotatable dose setting member with an outer surface and at least one axially oriented drive groove. The add-on device comprises a drive portion adapted to be mounted in engagement with the dose setting member and comprises a drive structure adapted to engage a drive groove and being biased in a radially inwards direction. This arrangement allows the drive structure to rotationally slide on the dose setting member outer surface and into engagement with the drive groove(s).

20 Claims, 27 Drawing Sheets

(52) U.S. Cl.
CPC .............. *A61M 2005/3126* (2013.01); *A61M 2205/3317* (2013.01); *A61M 2205/52* (2013.01)

(56) References Cited

U.S. PATENT DOCUMENTS

| | | | | |
|---|---|---|---|---|
| 2009/0318865 | A1* | 12/2009 | Moller | A61M 5/20 604/135 |
| 2014/0194826 | A1* | 7/2014 | Nielsen | G16H 20/17 604/189 |
| 2015/0018775 | A1* | 1/2015 | Groeschke | A61M 5/31568 604/207 |
| 2015/0202376 | A1* | 7/2015 | Haupt | A61M 5/31525 604/189 |
| 2015/0273163 | A1* | 10/2015 | Nielsen | A61M 5/31535 604/111 |
| 2015/0367077 | A1 | 12/2015 | Plambech et al. | |

FOREIGN PATENT DOCUMENTS

| | | | |
|---|---|---|---|
| CN | 104203315 B | | 7/2017 |
| EP | 3495008 A1 | * | 6/2019 |
| WO | 2008/037801 A1 | | 4/2008 |
| WO | 2010052275 A2 | | 5/2010 |
| WO | 2014020008 A1 | | 2/2014 |
| WO | 2014037331 A1 | | 3/2014 |
| WO | 2014161952 A1 | | 10/2014 |
| WO | 2016019856 A1 | | 2/2016 |
| WO | 2016087512 A1 | | 6/2016 |
| WO | 2016198516 A1 | | 12/2016 |
| WO | 2017186955 A1 | | 11/2017 |

* cited by examiner

ACCESSORY DEVICE WITH MOUNTING FEATURE FOR ENGAGING DIAL MEMBER

CROSS-REFERENCE TO RELATED APPLICATIONS

This application is a 35 U.S.C. § 371 National Stage application of International Application PCT/EP2019/053982 (published as WO 2019/162235), filed Feb. 18, 2019 which claims priority to European Patent Application 18157609.1, filed Feb. 20, 2018, the contents of all above-named applications are incorporated herein by reference.

The present invention generally relates to medical devices for which easy and efficient mounting and operation of a user-mountable add-on device is relevant.

BACKGROUND OF THE INVENTION

In the disclosure of the present invention reference is mostly made to drug delivery devices used e.g. in the treatment of diabetes by subcutaneous delivery of insulin, however, this is only an exemplary use of the present invention.

Drug delivery devices for subcutaneous injections have greatly improved the lives of patients who must self-administer drugs and biological agents. Such drug delivery devices may take many forms, including simple disposable devices that are little more than an ampoule with an injection means or they may be durable devices adapted to be used with prefilled cartridges. Regardless of their form and type, they have proven to be great aids in assisting patients to self-administer injectable drugs and biological agents. They also greatly assist care givers in administering injectable medicines to those incapable of performing self-injections. A common type of drug delivery devices allows a user to set a desired dose size for the drug to be delivered. For a typical mechanical device the dose setting means is in the form of a rotatable dose setting or dial member allowing the user to set (or "dial") the desired dose size which is then subsequently expelled from the device.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of injection information from medication delivery systems.

Though some injection devices integrate this monitoring/acquisition mechanism into the device itself, e.g. as disclosed in US 2009/0318865 and WO 2010/052275, most devices of today day are without it. The most widely used devices are purely mechanical devices being either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2014/037331 describes in a first embodiment an electronic supplementary device (also named "add-on module" or "add-on device") adapted to be releasably attached to a drug delivery device of the pen type. The device includes a camera and is configured to perform optical character recognition (OCR) on captured images from a rotating scale drum visible through a dosage window on the drug delivery device, thereby to determine a dose of medicament that has been dialed into the drug delivery device. WO 2014/020008 discloses an electronic supplementary device adapted to be releasably attached to a drug delivery device of the pen type. The device includes a camera and is configured to determine scale drum values based on OCR. To properly determine the size of an expelled dose the supplementary device further comprises additional electromechanical sensor means to determine whether a dose size is set, corrected or delivered. A further external device for a pen device is shown in WO 2014/161952.

When a given add-on device for a drug delivery device of the pen type is designed to cover the dose setting or dial member, the add-on device will typically comprise an outer "add-on dial member" which is then operated by the user, the outer dial member being rotationally coupled to the drug delivery device "inner" dial member. The rotational coupling would typically be based on a groves/splines interface between the drug delivery device dose dial and the add-on device directly or indirectly providing a rotational coupling between the two dial members. When a given add-on device is designed to be mounted on the drug delivery device in an axial direction, e.g. the add-on device comprises a bore adapted to receive a generally cylindrical portion of the drug delivery device, this would allow axially oriented spline coupling structures on the add-on device to engage corresponding axially oriented spline structures on the drug delivery device dial member. However, depending on the number of engaging spline structures a smaller or larger rotational orientation of the engaging parts relative to each other would be required during mounting of the add-on device. Addressing this issue WO 2016/198516 discloses an add-on device adapted to be mounted on the dose setting member of a pen type drug delivery device, the dose setting member comprising a number of circumferentially arranged axially oriented ribs intended to improve the user's grip on the dose setting member during setting of a dose. The add-on device comprises corresponding groove formations adapted to receive the ribs. To facilitate mounting, the groove formations are provided with distally facing funnel portions providing an amount of rotational force on the engaging structures during axial mounting of the add-on device, this helping the ribs of the dose setting member to be correctly received in the corresponding groove formations.

Having regard to the above, it is an object of the present invention to provide devices and methods allowing secure, easy and efficient mounting and operation of a drug delivery assembly comprising a user-mountable add-on device. The add-on device may be adapted to serve to determine the size of an expelled dose amount. Alternatively, the add-on device may be adapted to serve as an aid for people with impaired dexterity to set and release a dose of drug and thus dispense with any dose sensing and dose logging functionality.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first general aspect of the invention an assembly comprising a drug delivery device and an add-on device adapted to be releasably mounted thereon is provided. The drug delivery device comprises a housing defining a reference axis, a drug reservoir or means for receiving a drug reservoir, and drug expelling means comprising a relative to the reference axis rotatable dose setting member allowing a user to set a dose amount of drug to be expelled, the dose setting member being arranged at the proximal end of the housing and comprising a generally cylindrical outer surface with at least one axially oriented drive groove. The add-on device comprises a mounting portion adapted to be releasably attached to the drug delivery device housing in an axially non-moveable position, and a drive portion adapted to be mounted in engagement with the dose setting member, the drive portion comprising at least one drive structure adapted to engage a drive groove, each drive structure being biased in a radially inwards direction.

By this arrangement the drive portion can be mounted on the dose setting member in a rotationally non-engaged state with each drive structure in biased rotationally sliding engagement with the dose setting member outer surface, whereby the drive portion can be rotated into a rotationally locked state on the dose setting member when the at least one drive structure is aligned with a drive groove and biased into engagement therewith.

In this way an assembly is provided which allows easy, secure and efficient mounting and operation of a user-mountable add-on device on a drug delivery, the drug delivery device comprising a rotatable dose setting member being engaged and operated by the add-on device.

The mounting portion may be adapted to be mounted rotationally locked on the drug delivery device housing, with the drive portion being arranged to rotate relative to the mounting portion. For such an arrangement the add-on device may be provided with an add-on dose setting member being coupled to the mounting portion rotatable free but axially locked, and which is directly or indirectly rotationally coupled to the drive portion to thereby rotate the latter.

Alternatively the mounting portion may be adapted to be mounted rotationally free on the drug delivery device housing, with the mounting portion and the drive portion being rotationally locked to each other during dose setting.

The mounting portion and the drug delivery device housing may comprise inter-engaging releasable coupling means. In specific embodiments, the mounting portion and the housing comprise inter-engaging releasable coupling means allowing the add-on device to be mounted on the housing in one of one or more rotationally pre-determined positions.

In exemplary embodiments the add-on device comprises a bore adapted to axially receive a proximal portion of the drug delivery device. The drive portion may comprise a cylindrical member adapted to receive the dose setting member and be provided with at least one flexible structure forming the drive structure, e.g. in the form of a flexible finger with a free end portion forming the drive structure.

The drug delivery device may further comprise a release member actuatable between a proximal position and a distal position, the proximal position allowing a dose amount to be set, and the distal position allowing the drug expelling means to expel a set dose. Correspondingly, the add-on device may further comprise an add-on release member axially moveable relative to the add-on dose setting member between a dose setting state and a dose expelling state, wherein in a mounted state the add-on release member directly or indirectly engages and actuates the release member when moved distally.

In an exemplary embodiment, when the add-on release member is in the dose setting state, the add-on dose setting member and the drive member are rotationally coupled to each other, and, when the add-on release member is in the dose expelling state, the add-on dose setting member and the drive member have been rotationally de-coupled from each other.

In a further exemplary embodiment the drug delivery device comprises an indicator adapted to move during expelling of a dose amount, the amount of movement, e.g. rotation being indicative of the size of the expelled dose amount. Correspondingly, the add-on device comprises sensor means adapted to detect the amount of rotation of the indicator during expelling of a dose amount. The sensor means may be coupled non-rotationally to the drive portion.

The indicator may be arranged to rotate relative to the housing and corresponding to a reference axis and comprises a plurality of dipole magnets. The sensor means may comprise a plurality of magnetometers arranged non-rotational relative to the housing in a mounted state and adapted to determine magnetic field values from the plurality of dipole magnets, as well as processor means configured to determine on the basis of measured values from the plurality of magnetometers a rotational position and/or a rotational movement of the indicator.

By this arrangement a sensor assembly is provided in which external as well as internal magnetic disturbances can be cancelled out to a large extent by signal processing algorithms based on input from the rotating plurality of dipole magnets. In an exemplary embodiment the indicator element comprises two dipole magnets forming a quadrupole indicator element.

The rotational position and/or a rotational movement of the indicator element may be determined using a DFT algorithm. The sensor assembly may comprise a magnetisable component, e.g. in the form of a helical metal spring.

In an exemplary embodiment, and relative to the reference axis, the plurality of magnetometers is arranged in a proximal position, the magnetisable component is arranged in a distal position, and the indicator element is arranged in an intermediate position.

In a further aspect of the invention an add-on device adapted to be releasably mounted on a drug delivery device is provided. The drug delivery device comprises a housing defining a reference axis, a drug reservoir or means for receiving a drug reservoir, as well as drug expelling means comprising a relative to the reference axis rotatable dose setting member allowing a user to set a dose amount of drug to be expelled, the dose setting member being arranged at the proximal end of the housing and comprising a generally cylindrical outer surface with at least one axially oriented drive groove. Correspondingly, the add-on device comprises a mounting portion with a bore adapted to receive a portion of the drug delivery device housing and the dose setting member, and a drive portion adapted to be mounted in engagement with the dose setting member, the drive portion comprising at least one drive structure biased in a radially inwards direction, the at least one drive structure being adapted to be moved radially outwards when engaging a dose setting member. The drive portion may comprise a plurality of finger-like drive structures, e.g. 3, which may be oriented with the free ends in either a proximal or distal direction.

The disclosed add-on device may be modified corresponding to the above-described add-on device forming part of an assembly.

In a yet further aspect of the invention an add-on device adapted to be releasably mounted on a drug delivery device is provided. The drug delivery device comprises a device housing defining a reference axis and comprising a proximal portion, a drug reservoir or means for receiving a drug reservoir, and drug expelling means comprising a relative to the reference axis rotatable dose setting member allowing a user to set a dose amount of drug to be expelled, the dose setting member being arranged at the proximal end of the housing and comprising a generally cylindrical outer surface. The add-on device comprises an add-on housing comprising a distally facing cavity adapted to receive the drug delivery device housing proximal portion and being releasably attached thereto in an axially and rotationally non-moveable position, a gripping member arranged in the cavity and comprising a plurality of distal gripping arms having a radially open state allowing the drug delivery device housing proximal portion to be received, and a radially closed state allowing the gripping arms to engage the drug delivery device housing proximal portion, actuatable locking means for moving the gripping arms between the open and closed state, and a drive member adapted to receive the dose setting member and being releasably attached thereto in a rotationally non-moveable position. The add-on device has a reference axis coinciding with the drug delivery device reference axis. The gripping arms may be flexible allowing them to flex radially.

By this arrangement secure and user-friendly mounting of an add-on device on a drug delivery device is provided.

In an exemplary embodiment the gripping member is moveable relative to the add-on device housing between a distal receiving position and a proximal closed position, the locking means is actuated to move the gripping arms from the open to the closed state when the gripping member is moved from the distal to the proximal position, and the locking means is actuated to release the gripping arms when the gripping member is moved from the proximal to the distal position, this allowing the gripping arms to move radially to the open state.

The drive member and the gripping member may be axially coupled to each other. In an exemplary embodiment the gripping member comprises a distally facing coupling surface, and the drive member comprises a proximally facing coupling surface, wherein the two coupling surfaces are adapted to engage each other when the gripping member is moved distally relative to the add-on housing, the drive member thereby moving axially therewith. The two coupling surfaces may be inclined relative to a plane perpendicular to the reference axis, the inclination allowing the coupling surfaces to radially disengage.

The add-on device may be provided with a mounting coupling actuatable between a locked state in which the two coupling surfaces are prevented from moving radially relative to each other, and a released state in which the two coupling surfaces are allowed to move radially relative to each other, this introducing an amount of slack between the two surfaces. The mounting coupling may be designed to be released just prior to the gripping member being actuated to the closed state.

In an exemplary embodiment the add-on device comprises an add-on dose setting member being coupled to the add-on housing rotatable free, and which is directly or indirectly rotationally coupled to the drive member.

The add-on device may further comprise sensor means adapted to detect the amount of rotation of an indicator member relative to the add-on housing. The indicator may form part of the drug delivery device and be adapted to move during expelling of a dose amount, the amount of movement being indicative of the size of the expelled dose amount.

The indicator may be a magnetic member rotating during drug expelling, the amount of rotation being indicative of the size of the expelled dose amount. Alternatively, the indicator may be a component in a sound or vibration generating mechanism generating a sound or vibration pattern during drug expelling, the generated sound or vibration pattern being indicative of the size of the expelled dose amount. The indicator may be in the form of a drum with indicia rotating during drug expelling, the amount of rotation being indicative of the size of the expelled dose amount.

Alternatively, the indicator may form part of the drug delivery device and be adapted to move during dose setting, the amount of movement being indicative of the size of the set dose amount, e.g. the indicator may be in the form of the dose setting member.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin, however, the described module could also be used to create logs for other types of drug, e.g. growth hormone.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1A:
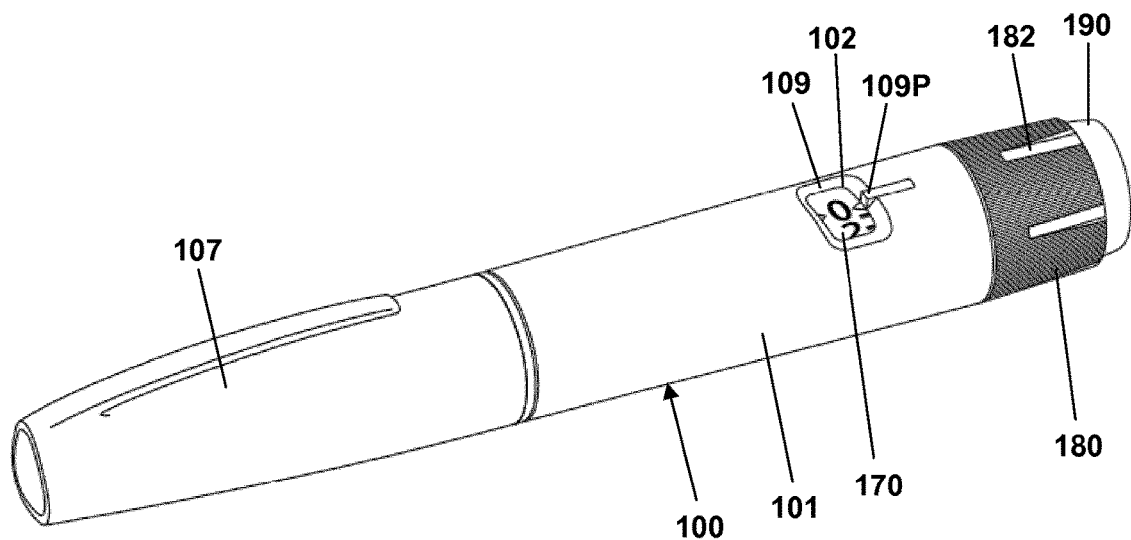
FIG. 1A shows a pen device.

Before turning to embodiments of the present invention per se, an example of a prefilled drug delivery will be described, such a device providing the basis for the exemplary embodiments of the present invention. Although the pen-formed drug delivery device 100 shown in FIGS. 1-3 may represent a "generic" drug delivery device, the actually shown device is a FlexTouch® prefilled drug delivery pen as manufactured and sold by Novo Nordisk A/S, Bagsvaerd, Denmark.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose setting member 180 with a number of axially oriented grooves 182 serves to manually set a desired dose of drug shown in display window 102 and which can then be expelled when the button 190 is actuated. As will be apparent from the below description, the shown axially oriented grooves 182 may be termed "drive grooves". The dose setting member 180 has a generally cylindrical outer surface 181 (i.e. the dose setting member may be slightly tapered) which in the shown embodiment is textured by comprising a plurality of axially oriented fine grooves to improve finger grip during dose setting. The window is in the form of an opening in the housing surrounded by a chamfered edge portion 109 and a dose pointer 109P, the window allowing a portion of a helically rotatable indicator member 170 (scale drum) to be observed. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
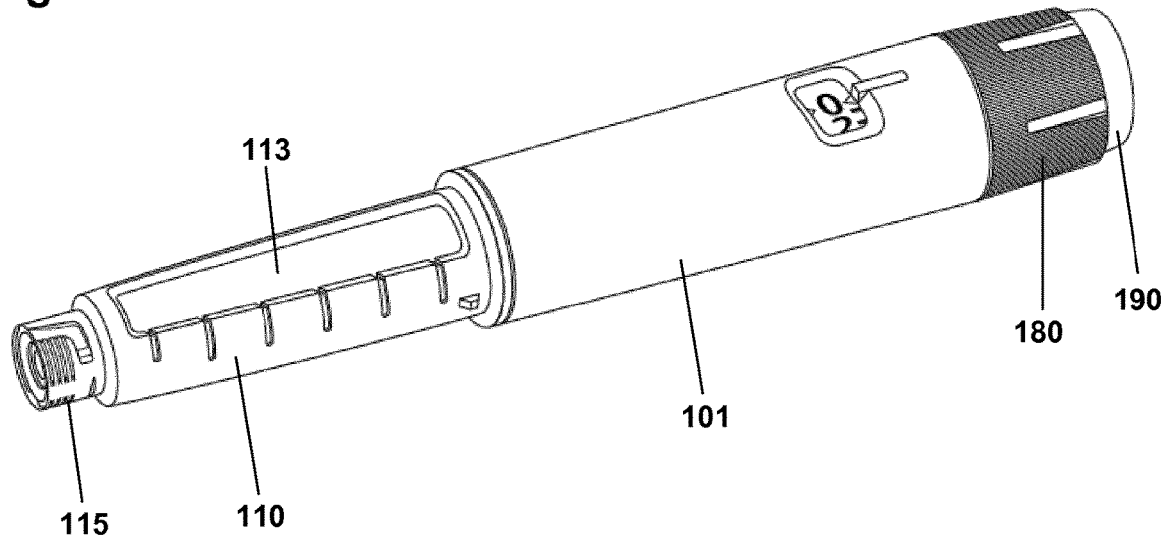
FIG. 1B shows the pen device of FIG. 1A with the pen cap removed.

Although FIG. 1 shows a drug delivery device of the prefilled type, i.e. it is supplied with a premounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "frontloaded" device in which a cartridge is inserted through a distal opening in the cartridge holder which is non-removable attached to the main part of the device.

As the invention relates to electronic circuitry adapted to interact with a drug delivery device, an exemplary embodiment of such a device will be described for better understanding of the invention.

Figure 2:
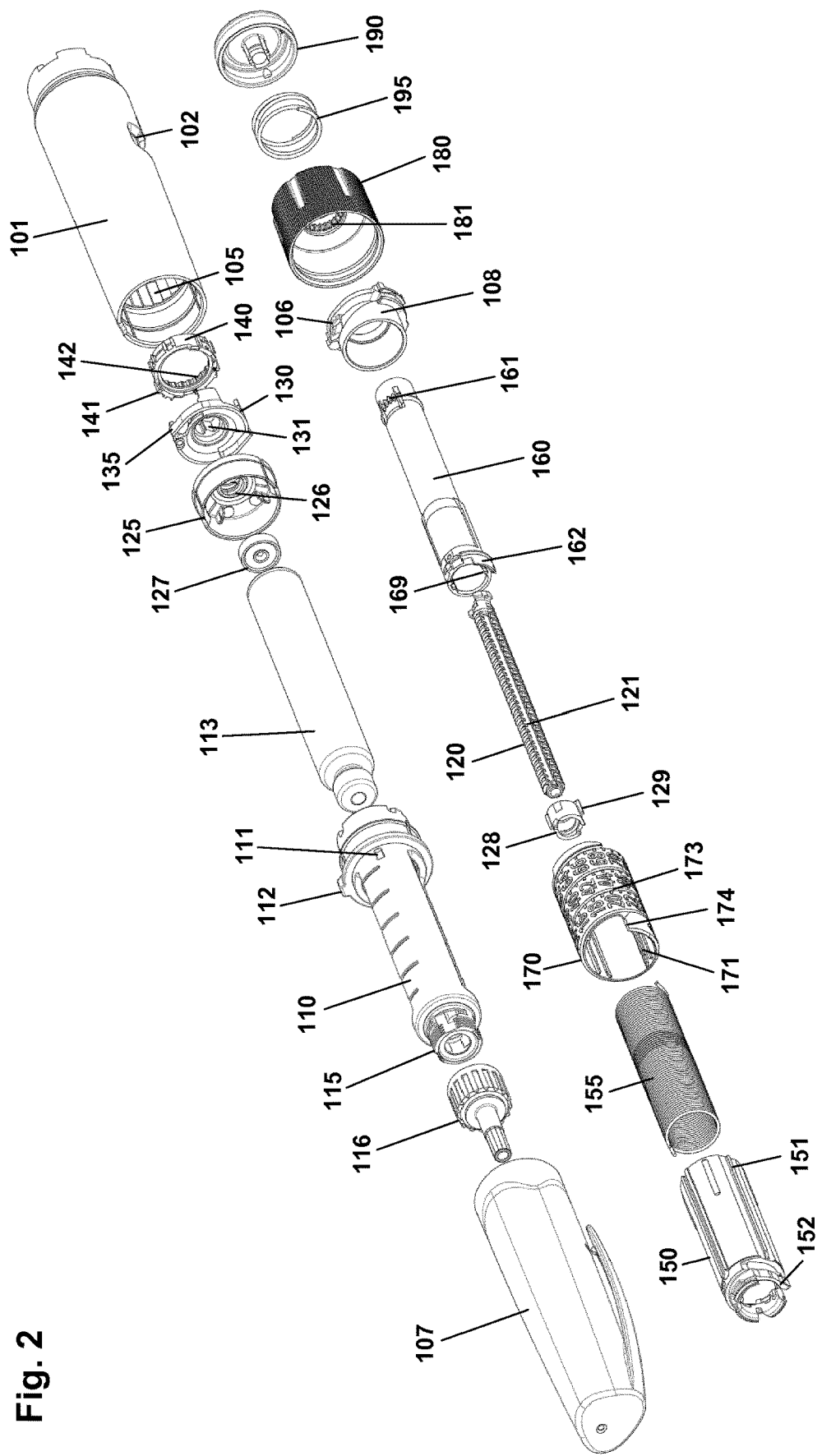
FIG. 2 shows in an exploded view the components of the pen device of FIG. 1A, FIGS. 3A and 3B show in sectional views an expelling mechanism in two states.

FIG. 2 shows an exploded view of the pen-formed drug delivery device 100 shown in FIG. 1. More specifically, the pen comprises a tubular housing 101 with a window opening 102 and onto which a cartridge holder 110 is fixedly mounted, a drug-filled cartridge 113 being arranged in the cartridge holder. The cartridge holder is provided with distal coupling means 115 allowing a needle assembly 116 to be releasably mounted, proximal coupling means in the form of two opposed protrusions 111 allowing a cap 107 to be releasable mounted covering the cartridge holder and a mounted needle assembly, as well as a protrusion 112 preventing the pen from rolling on e.g. a table top. In the housing distal end a nut element 125 is fixedly mounted, the nut element comprising a central threaded bore 126, and in the housing proximal end a spring base member 108 with a central opening is fixedly mounted. A drive system comprises a threaded piston rod 120 having two opposed longitudinal grooves and being received in the nut element threaded bore, a ring-formed piston rod drive element 130 rotationally arranged in the housing, and a ring-formed clutch element 140 which is in rotational engagement with the drive element (see below), the engagement allowing axial movement of the clutch element. The clutch element is provided with outer spline elements 141 adapted to engage corresponding splines 104 (see FIG. 3B) on the housing inner surface, this allowing the clutch element to be moved between a rotationally locked proximal position, in which the splines are in engagement, and a rotationally free distal position in which the splines are out of engagement. As just mentioned, in both positions the clutch element is rotationally locked to the drive element. The drive element comprises a central bore with two opposed protrusions 131 in engagement with the grooves on the piston rod whereby rotation of the drive element results in rotation and thereby distal axial movement of the piston rod due to the threaded engagement between the piston rod and the nut element. The drive element further comprises a pair of opposed circumferentially extending flexible ratchet arms 135 adapted to engage corresponding ratchet teeth 105 arranged on the housing inner surface. The drive element and the clutch element comprise cooperating coupling structures rotationally locking them together but allowing the clutch element to be moved axially, this allowing the clutch element to be moved axially to its distal position in which it is allowed to rotate, thereby transmitting rotational movement from the dial system (see below) to the drive system. The interaction between the clutch element, the drive element and the housing will be shown and described in greater detail with reference to FIGS. 3A and 3B.

On the piston rod an end-of-content (EOC) member 128 is threadedly mounted and on the distal end a washer 127 is rotationally mounted. The EOC member comprises a pair of opposed radial projections 129 for engagement with the reset tube (see below).

The dial system comprises a ratchet tube 150, a reset tube 160, a scale drum 170 with an outer helically arranged pattern forming a row of dose indicia, a user-operated dial member 180 for setting a dose of drug to be expelled, a release button 190 and a torque spring 155 (see FIG. 3). The dial member is provided with a circumferential inner teeth structure 181 engaging a number of corresponding outer teeth 161 arranged on the reset tube, this providing a dial coupling which is in an engaged state when the reset tube is in a proximal position during dose setting and in a disengaged state when the reset tube is moved distally during expelling of a dose. The reset tube is mounted axially locked inside the ratchet tube but is allowed to rotate a few degrees (see below). The reset tube comprises on its inner surface two opposed longitudinal grooves 169 adapted to engage the radial projections 129 of the EOC member, whereby the EOC can be rotated by the reset tube but is allowed to move axially.

The clutch element is mounted axially locked on the outer distal end portion of the ratchet tube 150, this providing that the ratchet tube can be moved axially in and out of rotational engagement with the housing via the clutch element. The dial member 180 is mounted axially locked but rotationally free on the housing proximal end, the dial ring being under normal operation rotationally locked to the reset tube (see below), whereby rotation of the dial ring results in a corresponding rotation of the reset tube 160 and thereby the ratchet tube. The release button 190 is axially locked to the reset tube but is free to rotate. A return spring 195 provides a proximally directed force on the button and the thereto mounted reset tube. The scale drum 170 is arranged in the circumferential space between the ratchet tube and the housing, the drum being rotationally locked to the ratchet tube via cooperating longitudinal splines 151, 171 and being in rotational threaded engagement with the inner surface of the housing via cooperating thread structures 103, 173, whereby the row of numerals passes the window opening 102 in the housing when the drum is rotated relative to the housing by the ratchet tube. The torque spring is arranged in the circumferential space between the ratchet tube and the reset tube and is at its proximal end secured to the spring base member 108 and at its distal end to the ratchet tube, whereby the spring is strained when the ratchet tube is rotated relative to the housing by rotation of the dial member. A ratchet mechanism with a flexible ratchet arm 152 is provided between the ratchet tube and the clutch element, the latter being provided with an inner circumferential teeth structures 142, each tooth providing a ratchet stop such that the ratchet tube is held in the position to which it is rotated by a user via the reset tube when a dose is set. In order to allow a set dose to be reduced a ratchet release mechanism 162 is provided on the reset tube and acting on the ratchet tube, this allowing a set dose to be reduced by one or more ratchet increments by turning the dial member in the opposite direction, the release mechanism being actuated when the reset tube is rotated the above-described few degrees relative to the ratchet tube.

Figure 3A:
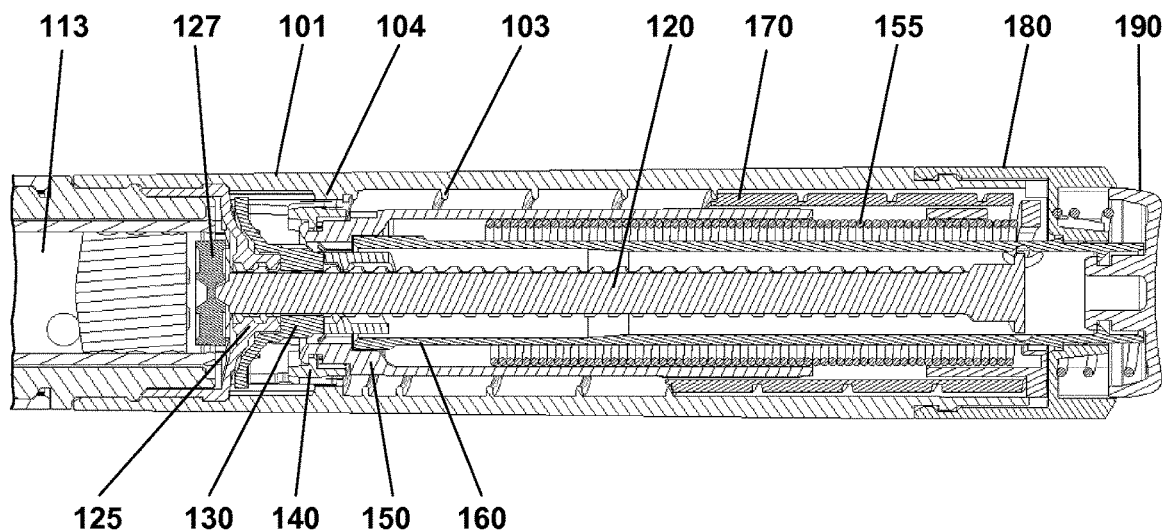

Having described the different components of the expelling mechanism and their functional relationship, operation of the mechanism will be described next with reference mainly to FIGS. 3A and 3B.

The pen mechanism can be considered as two interacting systems, a dose system and a dial system, this as described above. During dose setting the dial mechanism rotates and the torsion spring is loaded. The dose mechanism is locked to the housing and cannot move. When the push button is pushed down, the dose mechanism is released from the housing and due to the engagement to the dial system the torsion spring will now rotate back the dial system to the starting point and rotate the dose system along with it.

The central part of the dose mechanism is the piston rod 120, the actual displacement of the plunger being performed by the piston rod. During dose delivery, the piston rod is rotated by the drive element 130 and due to the threaded interaction with the nut element 125 which is fixed to the housing, the piston rod moves forward in the distal direction. Between the rubber piston and the piston rod, the piston washer 127 is placed which serves as an axial bearing for the rotating piston rod and evens out the pressure on the rubber piston. As the piston rod has a non-circular cross section where the piston rod drive element engages with the piston rod, the drive element is locked rotationally to the piston rod, but free to move along the piston rod axis. Consequently, rotation of the drive element results in a linear forwards movement of the piston. The drive element is provided with small ratchet arms 134 which prevent the drive element from rotating clockwise (seen from the push button end). Due to the engagement with the drive element, the piston rod can thus only move forwards. During dose delivery, the drive element rotates anti-clockwise and the ratchet arms 135 provide the user with small clicks due to the engagement with the ratchet teeth 105, e.g. one click per unit of insulin expelled.

Turning to the dial system, the dose is set and reset by turning the dial member 180. When turning the dial, the reset tube 160, the EOC member 128, the ratchet tube 150 and the scale drum 170 all turn with it due to the dial coupling being in the engaged state. As the ratchet tube is connected to the distal end of the torque spring 155, the spring is loaded. During dose setting, the arm 152 of the ratchet performs a dial click for each unit dialed due to the interaction with the inner teeth structure 142 of the clutch element. In the shown embodiment the clutch element is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 102.

The ratchet 152, 142 between the ratchet tube and the clutch element 140 prevents the spring from turning back the parts. During resetting, the reset tube moves the ratchet arm 152, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 142 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

Figure 3B:
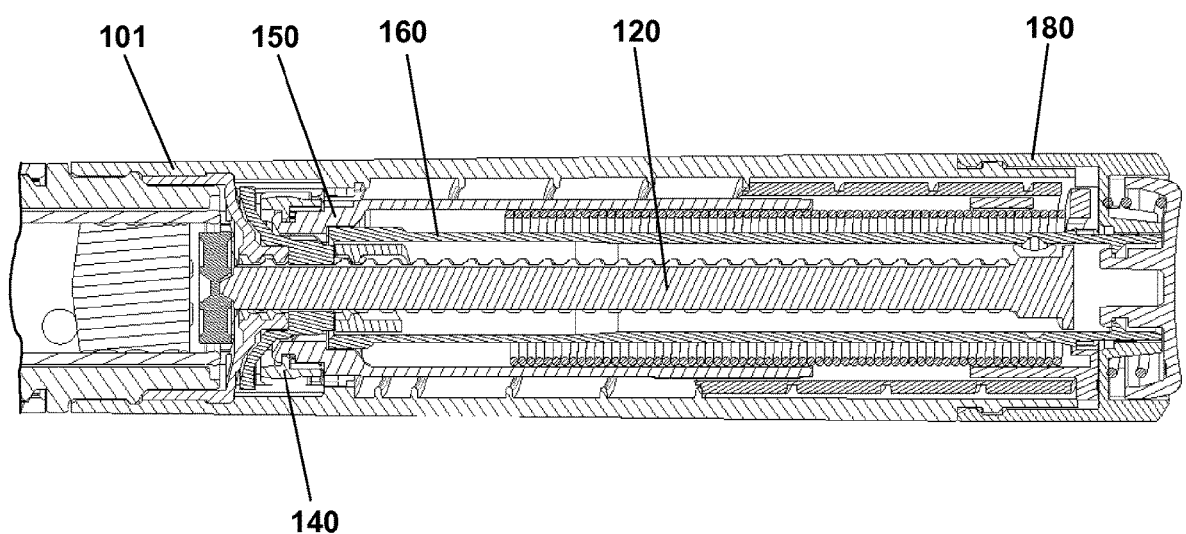

To deliver a set dose, the push button 190 is pushed in the distal direction by the user as shown in FIG. 3B. The dial coupling 161, 181 disengages and the reset tube 160 decouples from the dial member and subsequently the clutch element 140 disengages the housing splines 104. Now the dial mechanism returns to "zero" together with the drive element 130, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 128 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction, i.e. the now set dose corresponds to the remaining drug content in the cartridge.

The scale drum 170 is provided with a distal stop surface 174 adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 80 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism.

To prevent accidental over-dosage in case something should fail in the dialing mechanism allowing the scale drum to move beyond its zero-position, the EOC member serves to provide a security system. More specifically, in an initial state with a full cartridge the EOC member is positioned in a distal-most axial position in contact with the drive element. After a given dose has been expelled the EOC member will again be positioned in contact with the drive element. Correspondingly, the EOC member will lock against the drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm 106 on the spring base is forced backwards by the progressing scale drum. Just before "zero" the arm is released and the arm hits a countersunk surface on the scale drum.

The shown mechanism is further provided with a torque limiter in order to protect the mechanism from overload applied by the user via the dial member. This feature is provided by the interface between the dial member and the reset tube which as described above are rotationally locked to each other. More specifically, the dial member is provided with circumferential inner teeth structure 181 engaging a number of corresponding outer teeth 161, the latter being arranged on a flexible carrier portion of the reset tube. The reset tube teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth.

Having described the working principles of a mechanical drug delivery device, embodiments of the present invention will be described.

Figure 4A:
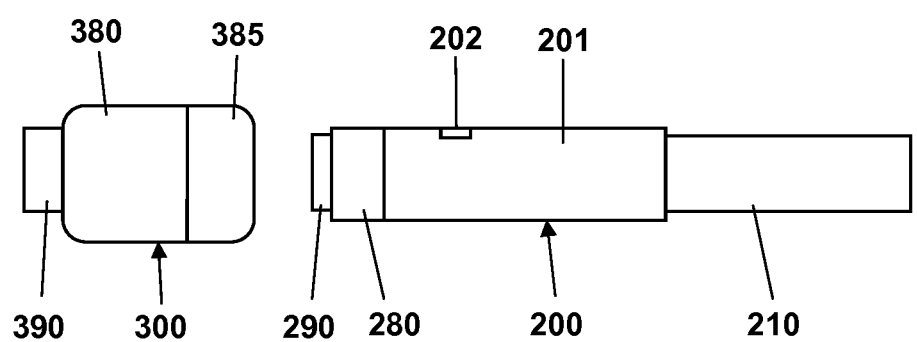
FIGS. 4A and 4B show a schematic representation of an add-on device and a drug delivery device.
Figure 4B:
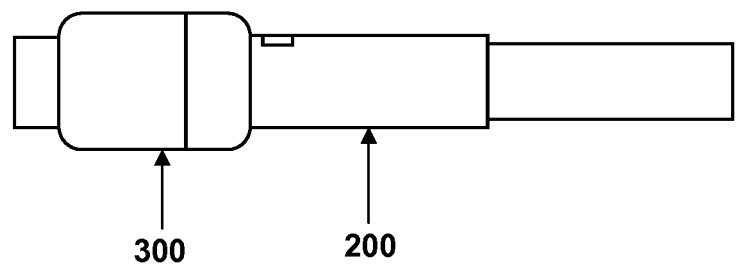

FIGS. 4A and 4B show a schematic representation of a first assembly of a pre-filled pen-formed drug delivery device 200 and a therefor adapted add-on dose logging device 300. The add-on device is adapted to be mounted on the proximal end portion of the pen device housing and is provided with dose setting and dose release means 380 covering the corresponding means on the pen device in a mounted state as shown in FIG. 4B. In the shown embodiment the add-on device comprises a coupling portion 385 adapted to be mounted axially and rotationally locked on the drug delivery housing. The add-on device comprises a rotatable dose setting member 380 which during dose setting is directly or indirectly coupled to the pen dose setting member 280 such that rotational movement of the add-on dose setting member in either direction is transferred to the pen dose setting member. In order to reduce influences from the outside during dose expelling and dose size determination, the outer add-on dose setting member 380 may be rotationally decoupled from the pen dose setting member 280 during dose expelling as will be described in greater detail with reference to the FIG. 5 embodiment. The add-on device further comprises a dose release member 390 which can be moved distally to thereby actuate the pen release member 290. As will be described in greater detail below with reference to FIG. 5 the add-on dose setting member gripped and rotated by the user may be attached directly to the pen housing in rotational engagement therewith.

Alternatively, the shown configuration may be adapted to serve primarily as an aid for people with impaired dexterity to set and release a dose of drug and thus dispense with any dose sensing and dose logging functionality. For such a configuration it is less important that the outer add-on dose setting member is rotationally decoupled from the pen dose setting member 280 during expelling of a dose. Correspondingly, the outer add-on dose setting member may be in permanent rotational engagement with the pen dose setting member 280.

Figure 5:
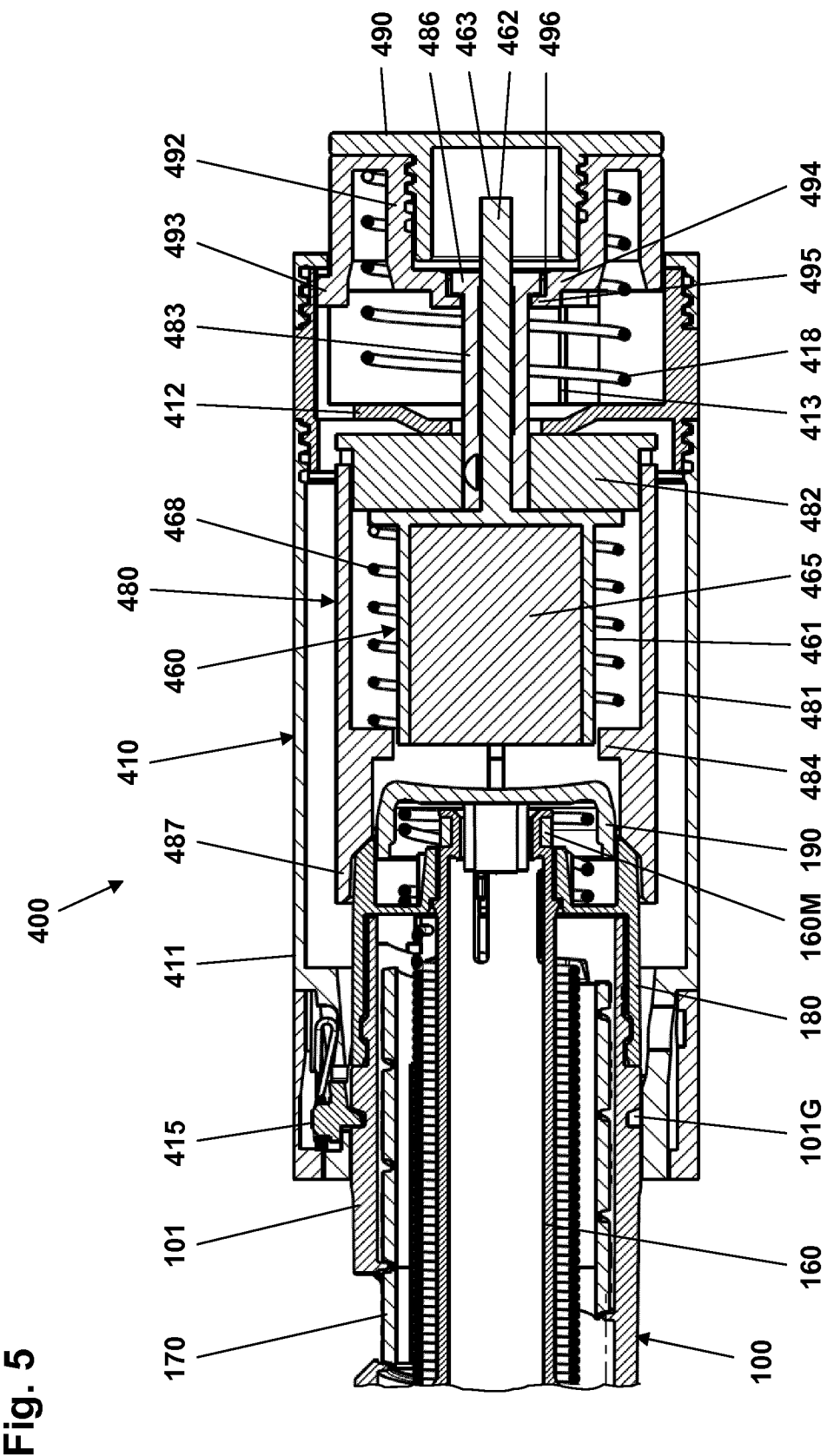
FIG. 5 shows in a cross-sectional view an add-on device mounted on the housing of a drug delivery device.

Turning to FIG. 5 a first exemplary embodiment of an add-on dose logging device 400 adapted to be mounted on a pen-formed drug delivery device 100 will be described in greater detail. The drug delivery device essentially corresponds to the drug delivery device described with reference to FIGS. 1-3 and thus comprises a housing 101, a rotatable dose setting member 180 allowing a user to set a dose amount of drug to be expelled, a release member 190 actuatable between a proximal dose setting position and a distal dose release position, a scale drum 170 as well as a reset tube 160. In order to cooperate with the add-on logging device the drug delivery device has been modified to comprise a generally ring-formed tracer magnet 160M attached to or formed integrally with the reset tube proximal end, the magnet serving as an indicator rotating during expelling of a dose amount, the amount of rotational movement being indicative of the size of the expelled dose amount. Further, the housing has been provided with a circumferential groove 101G just distally of the dose setting member serving as a coupling means for the add-on device.

The add-on device comprises an outer assembly 410 releasably attachable to the drug delivery device housing as well as an inner assembly 480. The inner and outer assemblies are rotationally locked to each other during dose setting, but rotationally de-coupled from each other during dose expelling. The shown embodiment is based on an experimental prototype for which reason some of the structures are formed from a number of assembled parts.

The outer assembly 410 comprises a generally cylindrical housing member 411 defining a general axis for the add-on device and serving as an add-on dose setting member, distally arranged coupling means 415 adapted to engage the coupling groove 101G of the pen housing, and a proximally arranged dose release member 490 coupled to the housing member 411 and axially moveable between an initial proximal position and an actuated distal position. In the shown embodiment the coupling means 415 is in the form of a number of spring-biased coupling members adapted to be releasable received in the housing groove 101G by snap action when the add-on device is slid over the proximal end of the drug delivery device 100, the coupling means thereby axially locking the add-on device to the pen device. The coupling means may be released by e.g. a pulling action or by actuation of a release mechanism. The housing comprises in the proximal portion an inner circumferential flange 412 and a number of axially oriented guide grooves 413. The dose release member 490 comprises a number of peripherally arranged axially oriented flanges 493 received in the guide grooves 413, the grooves providing a proximal stop against which the dose release member is biased by a first return spring 418 supported between the housing flange 412 and the dose release member 490. The dose release member comprises an inner cylindrical skirt portion 492 with a distal inner flange portion 494, the inner flange portion comprising a distal circumferential lip 495 and a proximal array of axially oriented locking splines 496.

The inner assembly 480 comprises an inner housing 481 and a therein arranged axially moveable sensor system in the form of a sensor module 460. The inner housing comprises a proximal wall portion 482 from which a hollow transmission tube 483 extends proximally, an inner circumferential flange portion 484 serving as support for a second biasing spring 468, and a distally extending circumferential skirt portion 487 provided with a number of axially oriented inner projections adapted to be received in the pen dose setting member drive grooves 182 (see FIG. 1A) to thereby rotationally lock the two members to each other, the engagement allowing some axial play during mounting and operation of the add-on device. Alternatively, the skirt portion 487 may be provided with radially inwardly biased drive structures of the type described below. The hollow tube 483 comprises at the proximal end a disc-formed portion having a distally facing stop surface adapted to engage the circumferential lip 495 and a circumferential array of axially oriented splines 486 adapted to engage the locking splines 496 on the dose release member 490 to thereby rotationally lock the inner assembly to the dose release member and thus the outer assembly.

The sensor module 460 comprises a sensor portion and a proximally extending actuation rod portion 462. The sensor portion comprises a generally cylindrical sensor housing 461 in which the electronic circuitry 465 is arranged (shown schematically in FIG. 5). The sensor housing comprises a distal actuation surface adapted to engage the pen actuation member 190. In the initial dose setting mode (i.e. with the dose release member 490 in the initial proximal position) the sensor housing is biased proximally by the second bias spring 468 into engagement with the inner housing proximal wall portion 482 and with the actuation rod 462 extending from the transmission tube 483 into the interior of the dose release member 490, an axial gap being formed between the proximal end 463 of the actuation rod and an inner actuation surface of the dose release member.

The electronic circuitry 465 comprises electronic components including processors means, one or more sensors, one or more switches, wireless transmitter/receiver means and an energy source. The sensors comprise one or more magnetometers adapted to measure a magnetic field generated by the pen tracer magnet 160M, this allowing rotational movement of the pen reset tube and thus the size of an expelled dose to be determined, see e.g. WO 2014/161952. Further sensor means may be provided allowing the type of the device to be recognized, e.g. a light emitter and a colour sensor adapted to determine the colour of the pen release member, the colour serving as an identifier for the drug type contained in the prefilled pen device. The processor means may be in the form of a generic microprocessor or an ASIC, non-volatile program memory such as a ROM providing storage for embedded program code, writable memory such as flash memory and/or RAM for data, and a controller for the transmitter/receiver.

In a situation of use with the add-on device 400 mounted on the pen drug delivery device 100 as shown in FIG. 5, the user starts setting a desired dose by rotating the housing member 411 (i.e. the add-on dose setting member) and with that also the dose release member 490. During dose setting the dose release member is biased towards its initial proximal position whereby it is rotationally locked to the inner assembly 480 via the locking splines 486, 496, this allowing the rotational movement of the add-on dose setting member to be transferred to the inner housing 461 and thus the pen dose setting member 180.

When a dose has been set the user will actuate the dose release member 490 by moving it distally against the force of the first bias spring 418. During the initial release movement the locking splines 486, 496 will disengage, this rotationally de-coupling the inner assembly 480 from the dose release member and thus from the add-on dose setting housing member 411. During the further release movement the dose release member 490 engages the actuation rod proximal end 463 whereby the sensor module 460 during the further release movement will be moved distally towards the pen dose release member 190 and subsequently into contact with the pen release member. The engaging surfaces of the actuation rod 462 and the add-on dose release member 490 are optimized for minimal transfer of rotational movement. Finally, further distal movement of the add-on release member 490 will result in actuation of the pen release member 190 and thereby expelling of the set dose, the sensor module 460 thereby serving as an actuator.

In order to determine the size of an expelled dose the amount of rotation of the tracer magnet 160M and thus the reset tube 160 is determined. More specifically, initial movement of the sensor module will activate a sensor switch (not shown) which in turn will activate the sensor electronics 465 and start sampling of data from the magnetometers, this allowing a rotational start position of the tracer magnet 160M to be determined prior to release of the expelling mechanism. During this period also the colour of the pen release member and thus the type of drug contained in the cartridge may be determined. As the reset tube may rotate more than 360 degrees during expelling of a dose of drug, rotational movement during expelling will be detected and the number of full rotations (if any) determined. When it is detected that rotation of the reset tube has stopped, e.g. when a set dose has been fully expelled or when out-dosing is paused by the user, a rotational end position will be determined, this allowing the size of an expelled dose to be determined. Alternatively, the rotational end position may be determined when the sensor switch detects that the sensor module 460 has returned to its initial position.

As appears, due to the rotational un-coupling of the inner assembly 460 from the outer assembly 480 during drug expelling, it is prevented to a high degree that movements of the outer parts of the add-on device will negatively influence the precise determination of rotational movement and rotational positions of the reset tube 160.

The determined dose size will be stored together with a time stamp and, if detected, a drug type identifier in a log memory. The content of the log memory may then be transmitted by NFC, Bluetooth® or other wireless means to an external device, e.g. a smartphone, which has been paired with the add-on logging device. An example of a suitable pairing process is described in EP application 17178059.6 which is hereby incorporated by reference.

Figure 6:
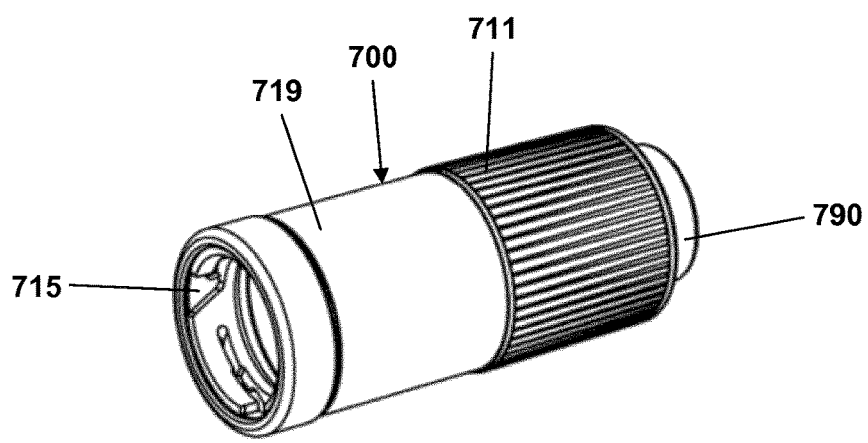
FIG. 6 shows a second embodiment of add-on device in combination with a drug delivery device.
Figure 6:
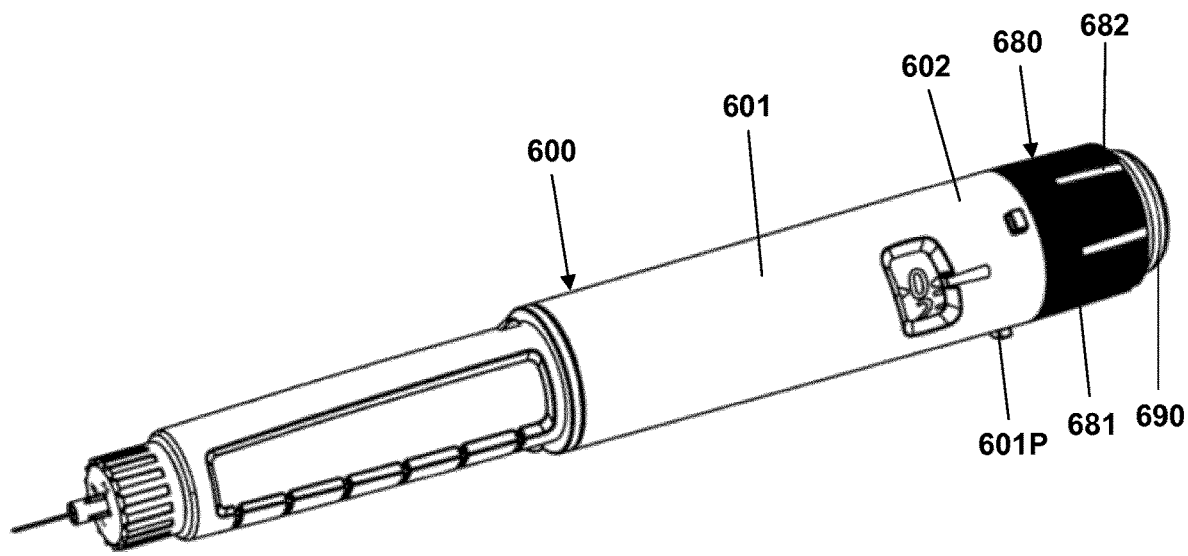

Turning to FIG. 6 a second exemplary embodiment of an add-on dose logging device 700 adapted to be mounted on a pen-formed drug delivery device 600 will be described in greater detail. The drug delivery device essentially corresponds to the drug delivery devices described with reference to FIGS. 1-3 and thus comprises a housing 601, a rotatable dose setting member 680 allowing a user to set a dose amount of drug to be expelled, a release member 690 actuatable between a proximal dose setting position and a distal dose release position, a scale drum 670 as well as a reset tube 660. In order to cooperate with the add-on logging device 700 the drug delivery device has been modified to comprise a generally ring-formed magnet 660M attached to or formed integrally with the reset tube proximal end, the magnet serving as an indicator rotating during expelling of a dose amount, the amount of rotational movement being indicative of the size of the expelled dose amount. Further, the housing proximal portion 602 has been provided with a number of protuberances 601P just distally of the dose setting member serving as a coupling means for the add-on device. In the shown embodiment three coupling protrusions are located equidistantly on the housing.

The add-on device 700 comprises an outer assembly 710 releasably attachable to the drug delivery device housing as well as an inner assembly (see below). The outer assembly 710 comprises a generally cylindrical distal coupling portion 719 (as in the embodiment of FIG. 4A) defining a general axis for the add-on device, the coupling portion having a generally cylindrical bore adapted to receive a corresponding generally cylindrical coupling portion of the drug delivery pen and being adapted to be mounted axially and rotationally locked on the drug delivery housing by means of a number of bayonet coupling structures 715 adapted to engage the corresponding coupling protuberances 601P on the pen housing and releasably snap into engagement. The add-on device further comprises a proximal dose setting member 711 mounted freely rotatable on the coupling portion and which like in the embodiment of FIG. 5 is coupled to the pen dose setting member 680 such that rotational movement of the add-on dose setting member 711 in either direction is transferred to the pen dose setting member. The add-on device further comprises a dose release member 790 which during dose setting rotates with the dose setting member. A first biasing spring 718 supported on an inner circumferential flange 712 on the dose setting member provides a proximally directed biasing force on the dose release member. As in the embodiment of FIG. 5 the inner and outer assemblies are rotationally locked to each other during dose setting, but rotationally decoupled from each other during dose expelling.

The inner assembly 780 generally corresponds to the inner assembly 480 of the FIG. 5 embodiments and thus generally comprises the same structures providing the same functionality. Correspondingly, the inner assembly comprises (see FIG. 7A) an inner housing 781 and a therein arranged axially moveable sensor module 760. The inner housing comprises a proximal wall portion 782 from which a hollow transmission tube structure 783 extends proximally, a distal inner circumferential flange portion 784 serving as support for a second biasing spring 768, and a distally extending circumferential skirt portion 787 adapted to engage the pen dose setting member drive grooves 682 (see FIG. 6) to thereby rotationally lock the two members to each other, the engagement allowing some axial play during mounting and operation of the add-on device. In the shown embodiment the structures engaging the dose setting member drive grooves 682 are in the form of flexible fingers 751 allowing for ease of mounting as will be described in greater detail below. The fingers may as shown be mounted to the skirt portion 787, e.g. formed as part of a sheet metal member, or they may be formed integrally with the skirt portion. The hollow tube 783 comprises at the proximal end a number of flange portions 788 having distally facing stop surfaces adapted to engage a circumferential inner flange 795 of the dose release member 790, as well as a number of axially oriented splines adapted to engage the locking splines 796 on the dose release member 790 to thereby rotationally lock the inner assembly to the dose release member and thus the outer assembly.

The sensor module 760 comprises a sensor portion and a proximally extending actuation rod portion 762. The sensor portion comprises a generally cylindrical sensor housing 761 in which the electronic circuitry 765 (see below) is arranged. The sensor housing comprises a distal spacer cap 764 covering the magnet sensors and being adapted to engage the pen actuation member 690. In the initial dose setting mode (i.e. with the dose release member 790 in the initial proximal position) the sensor housing is biased proximally by the second bias spring 768 into engagement with the inner housing proximal wall portion 782 and with the actuation rod 762 extending from the transmission tube 783 into the interior of the dose release member 790, an axial gap being formed between the proximal end 763 of the actuation rod and an inner actuation surface of the dose release member.

The electronic circuitry 765 comprises electronic components including processor means, sensors, an activation switch, e.g. a dome switch actuated by an axial force exerted on the actuation rod portion 762, wireless transmitter/receiver means and an energy source. More specifically, in the shown embodiment the electronic circuitry 765 comprises a layered construction comprising, from the distal end, a first PCB 766A on which a number of sensor components, e.g. magnetometers 766M, are arranged, a pair of battery connector discs 766B for a pair of coin cells, a second PCB 766C on which the majority of the electronic components are mounted (e.g. processor, transmitter/receiver and memory), and an upper disc 766D with a slot allowing the actuation rod portion 762 to contact and actuate a PCB mounted activation switch 766S, the five members being interconnected by flexible ribbon connectors.

The sensors comprise a number of magnetometers adapted to measure a magnetic field generated by the pen magnet 660M, this allowing rotational movement of the pen reset tube and thus the size of an expelled dose to be determined, see e.g. WO 2014/0161952. Further sensor means may be provided allowing the type of the device to be recognized, e.g. a light emitter and a colour sensor adapted to determine the colour of the pen release member, the colour serving as an identifier for the drug type contained in the prefilled pen device. The colour sensor and light emitter may operate with visible (to the human eye) light or light fully or partly outside the visible spectrum. The processor means may be in the form of a generic microprocessor or an ASIC, non-volatile program memory such as a ROM providing storage for embedded program code, writable memory such as flash memory and/or RAM for data, and a controller for the transmitter/receiver.

In a situation of use with the add-on device 700 mounted on the pen drug delivery device 600, the user starts setting a desired dose by rotating the dose setting member 711 (i.e. the add-on dose setting member) and with that also the dose release member 790. During dose setting the dose release member is biased towards its initial proximal position whereby it is rotationally locked to the inner assembly 780 via the locking splines 786, 796, this allowing the rotational movement of the add-on dose setting member to be transferred to the inner housing 761 and thus the pen dose setting member 680.

When a dose has been set the user will actuate the dose release member 790 by moving it distally against the force of the first bias spring 718. During the initial release movement the locking splines 786, 796 will disengage, this rotationally de-coupling the inner assembly 780 with the electronics from the dose release member 790 and thus from the add-on dose setting member 711. During the further release movement the dose release member 790 engages the actuation rod proximal end 763 (see FIG. 8A) whereby the sensor module 760 during the further release movement will be moved distally towards the pen release member 690 and subsequently into contact with the pen release member (see FIG. 8B). The engaging surfaces of the actuation rod 762 and the add-on dose release member 790 are optimized for minimal transfer of rotational movement. Finally, further distal movement of the add-on release member 790 will result in actuation of the pen release member 690 (see FIG. 8C in which the reset tube outer teeth 661 has been moved distally) and thereby expelling of the set dose (see FIG. 8D), the sensor module 760 thereby serving as an actuator.

In order to determine the size of an expelled dose the amount of rotation of the magnet 660M and thus the reset tube 660 is determined. More specifically, initial movement of the sensor module will activate a sensor switch which in turn will activate the sensor electronics 765 and start sampling of data from the magnetometers, this allowing a rotational start position of the magnet 660M to be determined prior to release of the expelling mechanism. During this period also the colour of the pen release member and thus the type of drug contained in the cartridge may be determined. As the reset tube 660 may rotate more than 360 degrees during expelling of a dose of drug, rotational movement during expelling will be detected and the number of full rotations (if any) determined. When it is detected that rotation of the reset tube has stopped, e.g. when a set dose has been fully expelled or when out-dosing is paused by the user, a rotational end position will be determined, this allowing the size of an expelled dose to be determined. Alternatively, the rotational end position may be determined when the sensor switch detects that the sensor module 760 has returned to its initial position.

As appears, due to the rotational un-coupling of the inner assembly 760 from the outer assembly 780 during drug expelling, it is prevented to a high degree that movements of the outer parts of the add-on device will negatively influence the precise determination of rotational movement and rotational positions of the reset tube 660.

Figure 9:
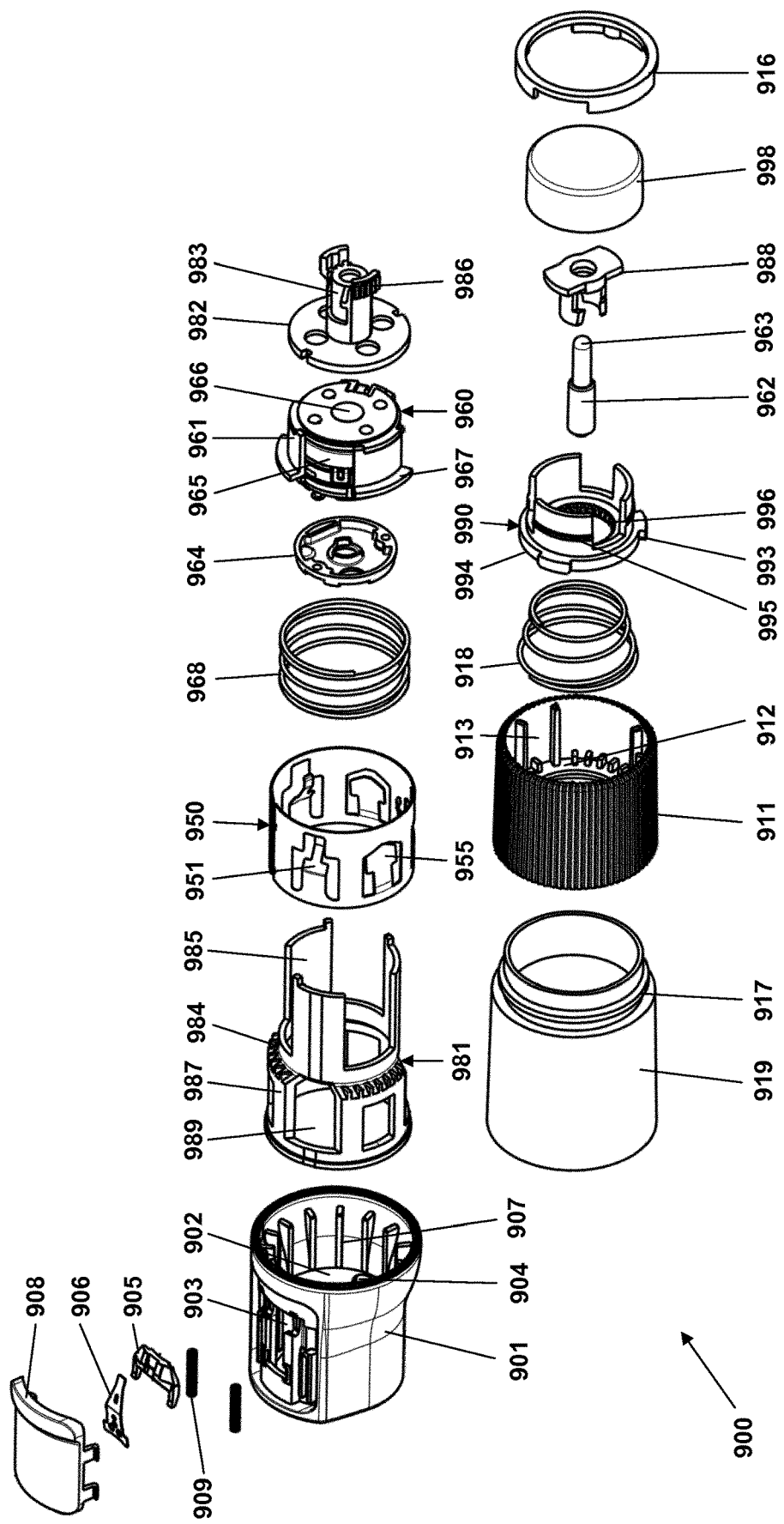
FIG. 9 shows in exploded view components of a third embodiment of an add-on device.

Turning to FIG. 9 a third exemplary embodiment of an add-on dose logging device 900 adapted to be mounted on a pen-formed drug delivery device 800 will be described in greater detail. The slightly modified drug delivery pen device 800 will be described with reference to FIGS. 10A and 10B.

Figure 7A:
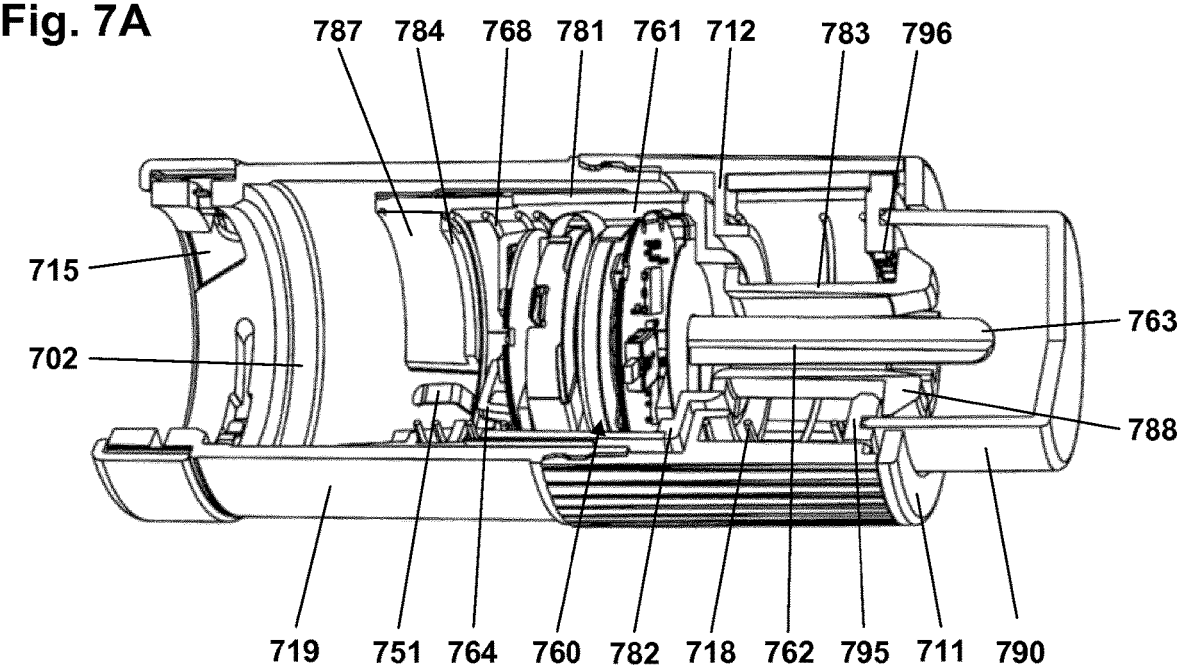
FIGS. 7A and 7B show cross-sectional views of the add-on device of FIG. 6.
Figure 7B:
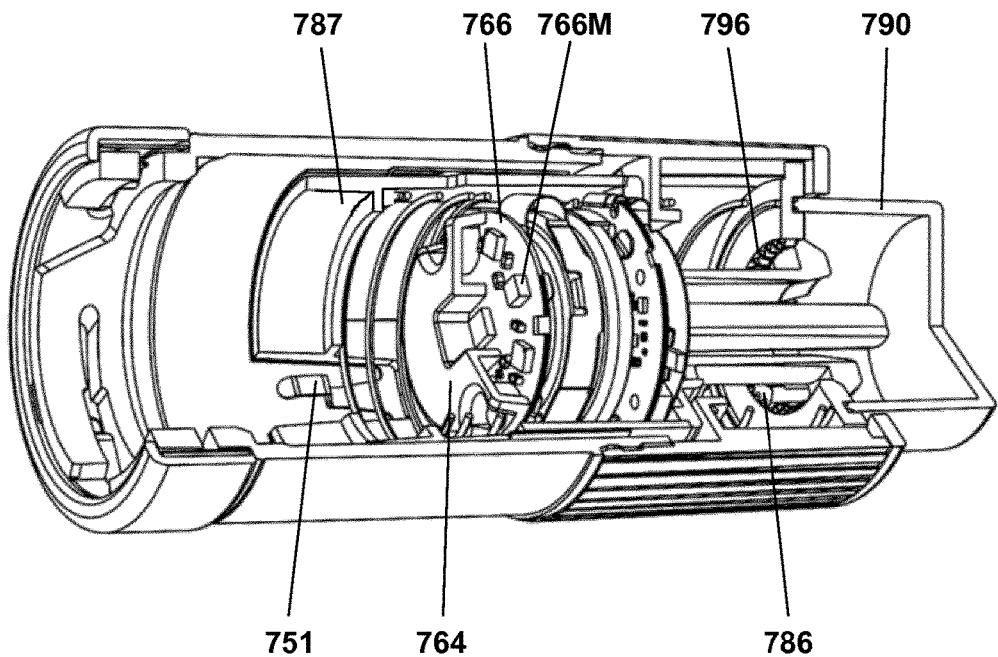
Figure 7C:
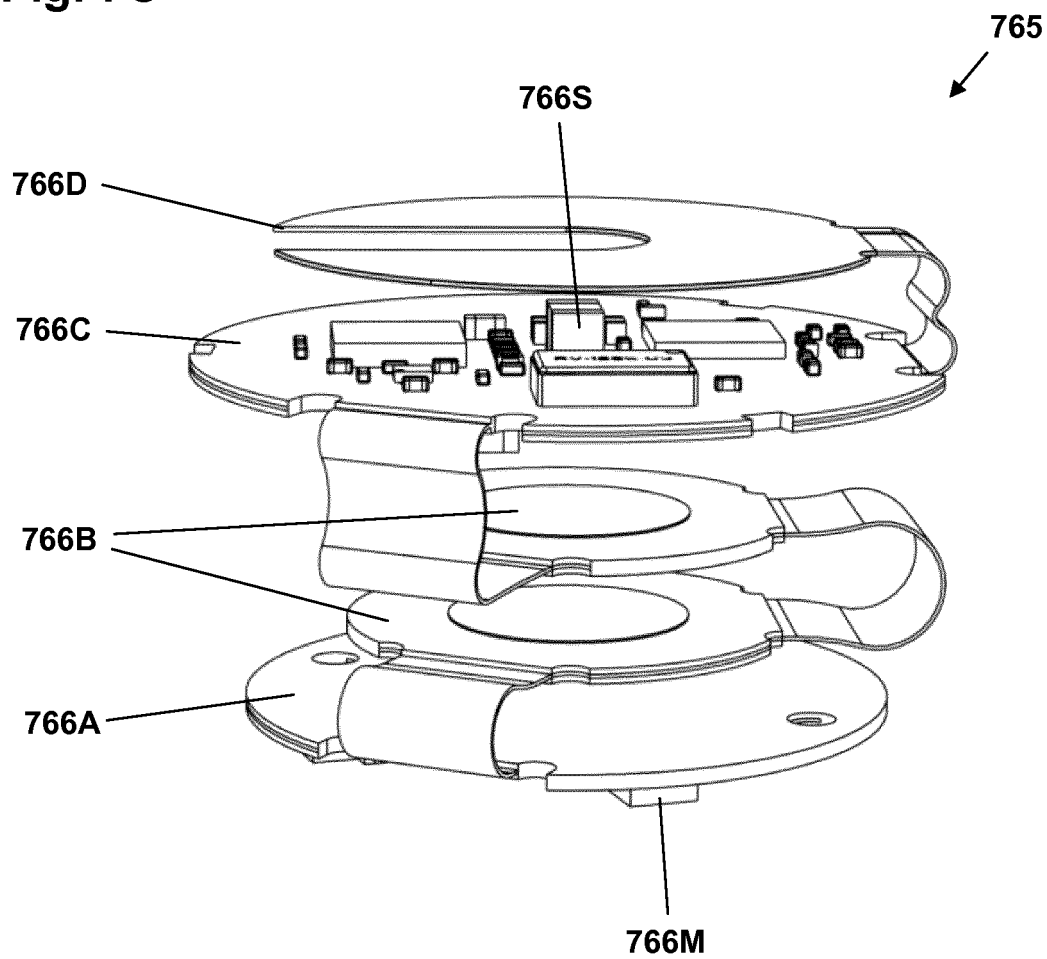
FIG. 7C shows in detail the electronic sensor circuitry incorporated in the add-on device of FIG. 7A, FIGS. 8A-8D show in sectional views and in different operational states an assembly comprising the add-on device of FIG. 6 mounted on a drug delivery device.

The add-on dose logging device 900 essentially corresponds to the add-on dose logging device 600 described with reference to FIGS. 6-8 and thus comprises an outer assembly releasably attachable to the drug delivery device housing, an inner assembly with a sensor module as well as a release member assembly. In contrast to the above described embodiments, the exploded view of FIG. 9 shows the individual components from which the assemblies are formed.

The outer assembly is formed by a distal housing coupling portion 901, a thereto attachable proximal housing portion 919, an add-on dose setting member 911 adapted to be mounted freely rotatable on the proximal housing portion, and a locking ring 916 adapted to be mounted in the dose setting member to enclose the release member assembly. A locking assembly comprises a release slider 908, a catch member 905, a bias spring 906 as well as a pair of return coil springs 909 for the slider, the locking assembly components being adapted to be mounted in the housing coupling portion 901.

More specifically, the distal housing coupling portion 901 comprises a cylindrical bore 902 adapted to receive a corresponding cylindrical coupling portion of the drug delivery pen device in a snug fit (see below). The bore is provided with a distally facing and axially oriented groove adapted to receive a pen housing locking protuberance 805 when the add-on device is axially mounted on the pen device. The proximal portion of the distal housing coupling portion tapers outwardly to a larger diameter and comprises a plurality of longitudinal ribs 907 each having a proximally facing end surface, the end surfaces serving as a distal stop for the inner assembly. The coupling portion 901 is adapted to cover the pen device display window when mounted and thus comprises a window opening 904 allowing the display window and thus the scale drum to be observed. Opposite the window opening a second opening 903 is provided adapted to receive the locking assembly components. The catch member 905 is pivotably mounted in the second opening and biased inwards by bias spring 906, this allowing the catch member to snap in place distally of the pen housing locking protuberance 805 when the add-on device is axially mounted on the pen device. As the locking means is arranged opposite the window opening 904 it is assured that the user can easily orient the add-on device rotationally during mounting. The release slider 908 is slidingly mounted in the second opening and biased in the distal direction by the return springs 909. When the user moves the release slider proximally this lifts the catch member 905 out of engagement with the housing locking protuberance 805 allowing the add-on device to be moved proximally and thus to be removed from the pen device. The proximal housing portion 919 is fixedly attached to the coupling portion 901 by e.g. welding, adhesive or snap means, and comprises a circumferential ridge 917 allowing the dose setting member 911 to be mounted freely rotatable by snap action. The dose setting member comprises a circumferential inner flange 912 which in an assembled state serves as a proximal stop for the inner assembly and a distal stop for the release member return spring 918, as well as a number of axially extending inner flanges forming a number of guide tracks 913 for the release member assembly. The locking ring 916 is adapted to be mounted axially fixed in the dose setting member by e.g. welding, adhesive or snap means as shown to thereby seal the gap between the dose setting member 911 and the cap member 998.

The inner assembly comprises a generally cylindrical inner housing member 981, a cylindrical locking member 950 adapted to be mounted on the inner housing member, and a proximal wall or lid member 982 adapted to be attached to the inner housing member to enclose the therein mounted sensor module. The wall member comprises a proximally extending tube portion 983 adapted to receive a proximal flange member 988.

More specifically, the inner housing member 981 comprises a larger diameter distal skirt portion 987 with a number of openings 989, a smaller diameter proximal portion with a number of axially extending wall sections 985 forming a number of guide tracks for the sensor module. The transition between the two portions forms an outer circumferential distal support 984 for a sensor spring 968 (see below). In the shown embodiment the cylindrical locking member 950 is formed from a single piece of sheet metal wherein is formed a first plurality of axially extending flexible dial locking arms 951 each having a proximal free end portion extending radially inwards, and a second plurality of axially extending flexible mounting arms 955 each having a proximal free end portion extending radially inwards. The mounting arms serve to snap into engagement with corresponding mounting openings 989 when the locking member is mounted on the inner housing member 981, this axially and rotationally locking the two members. The dial locking arms 951 distal ends are inwardly rounded and adapted to engage the pen dose setting member drive grooves 882 (see below). The proximal wall member 982 is adapted to be fixedly attached to the inner housing flanges by e.g. welding, adhesive or snap means and serves in an assembled state as a proximal stop for the sensor module. The proximally extending tube portion 983 comprises at the proximal end a pair of opposed radial extensions each comprising a plurality of axially oriented locking splines 986 adapted to engage corresponding splines on the release member in an assembled state. The proximal flange member 988 is adapted to be fixedly attached to the tube portion 983 by e.g. welding, adhesive or snap means as shown. The flange member comprises a central bore with a diameter smaller than the distal larger diameter end of the actuation rod 962 (see below), this providing a proximal stop for the actuation rod.

The sensor module 960 comprises a generally cylindrical sensor housing 961 in which electronic circuitry 965 with distally facing sensor components is mounted, a spacer cap 964 adapted to be mounted on the sensor module housing distal end to cover and enclose the sensor components, as well as an actuation rod 962 adapted to be arranged in the wall member tube portion 983. A sensor module return spring 968 is adapted to be arranged between the inner housing member 981 and the sensor housing 961 to provide a proximally directed biasing force on the sensor module.

Figure 13A:
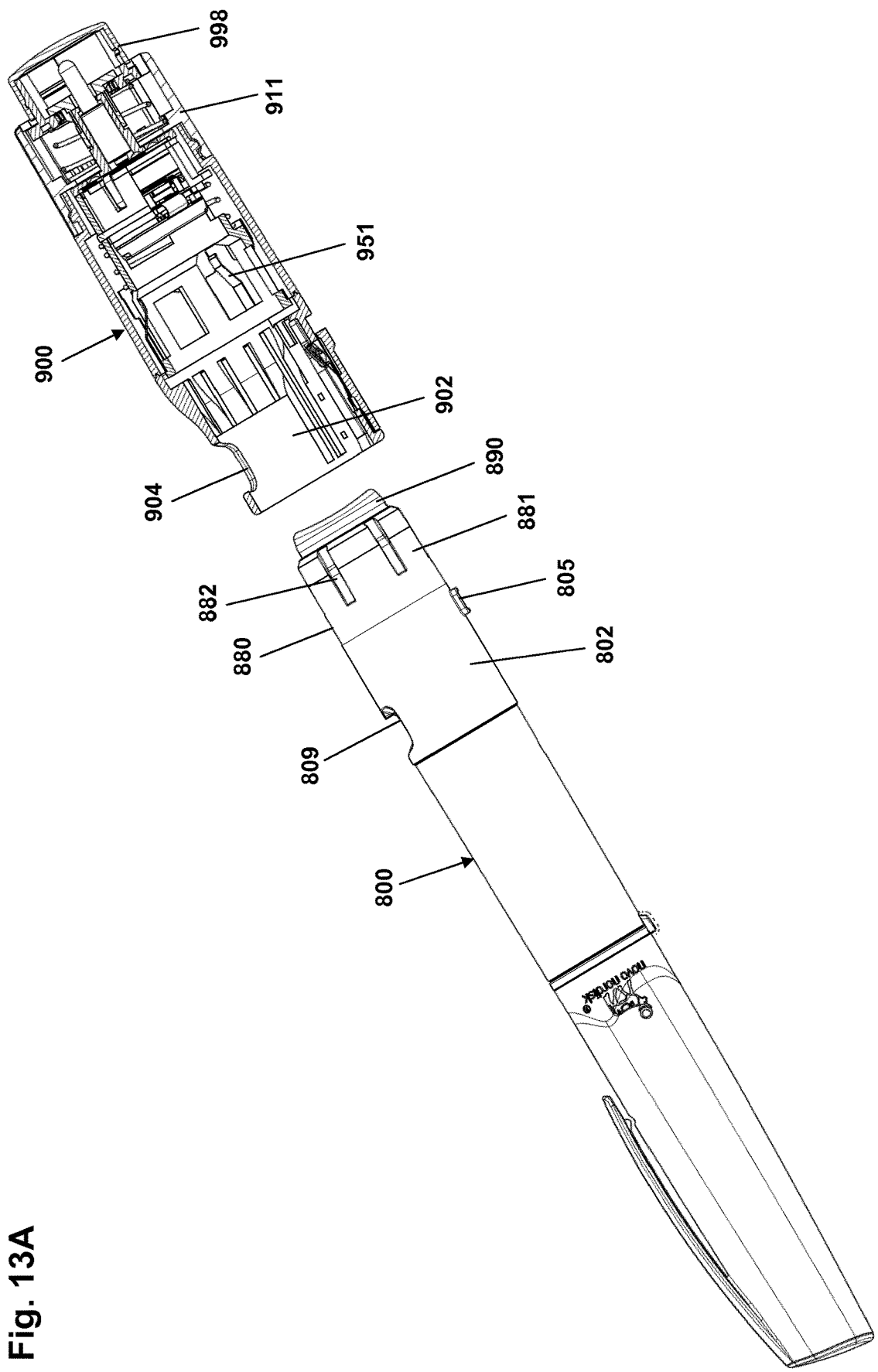
FIGS. 13A-13F show in cross-sectional views the third embodiment in a series of operational states.

More specifically, the spacer cap 964 is adapted to be fixedly attached to the sensor housing by e.g. welding, adhesive or snap means and serves in an assembled state to protect the sensor components and as a distally facing contact surface adapted to engage the pen device release member 890 (see FIG. 13A). The sensor housing comprises a number of radially protruding distal and proximal guide flanges 967 adapted to be received non-rotationally but axially free in the inner housing member guide tracks. The distal guide flanges also provide a proximal stop surface for the sensor spring 968. A distal stop for the sensor module is provided by the inner housing corresponding to the distal end of the guide tracks and/or the compressed sensor spring. The actuation rod 962 comprises a larger diameter distal portion allowing the rod to be freely received in the tube portion 983 and a smaller diameter proximal portion adapted to protrude through the bore in the flange member 988. The actuation rod comprises a rounded proximal end 963, the engaging surfaces of the actuation rod and the cap member 998 being optimized for minimal transfer of rotational movement. The sensor module comprises a proximally facing centrally arranged actuation switch 966, e.g. a dome switch, adapted to be actuated by the actuation rod.

The release member assembly comprises a body member 990 and a thereon mountable cap member 998. A release member return spring 918 is adapted to be arranged between the dose setting member flange 912 and the release body member 990 to provide a proximally directed biasing force on the release body member.

More specifically, the release body member 990 comprises a distal ring portion 994 with an inner circumferential array of axially oriented splines 996 adapted to engage the locking splines 986 on the tube portion 983 in an assembled state, as well as a number of radially protruding guide flanges 993 adapted to be received non-rotationally but axially free in the dose setting member guide tracks 913. The cap member 998 is adapted to be axially fixedly attached to the body member by e.g. welding, adhesive or snap means 995 as shown. In an assembled state flange member 988 serves as a proximal stop for the release body member 990 and the release member return spring 918 acts on the ring portion distal surface.

Figure 10A:
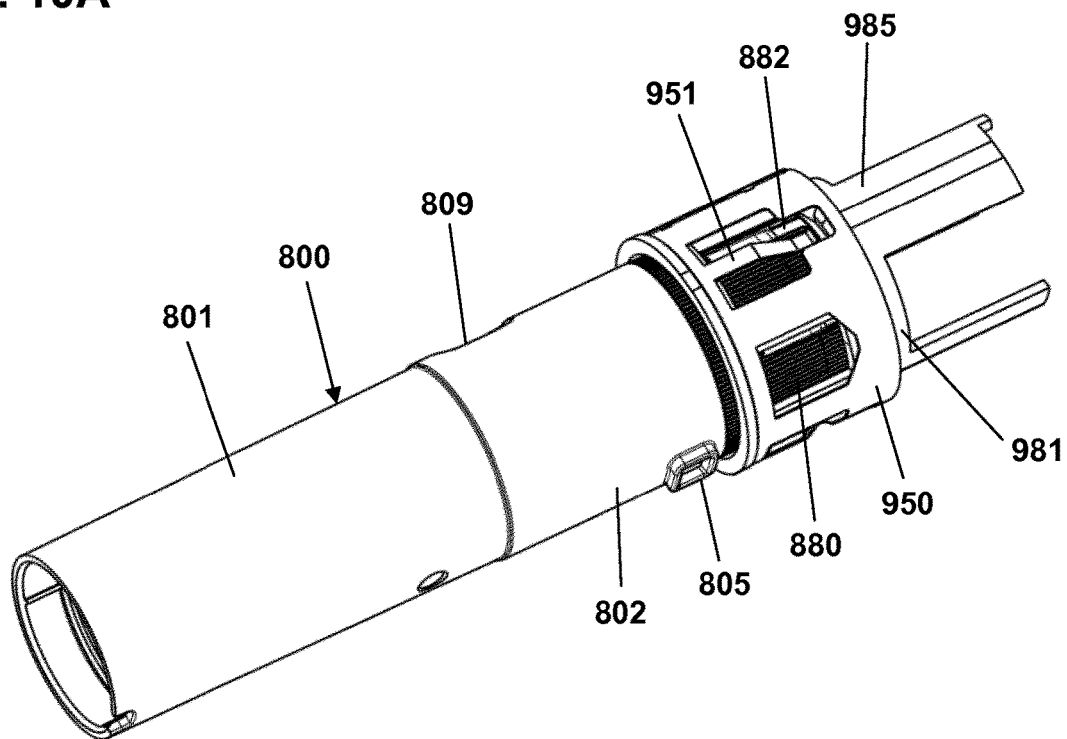
FIGS. 10A and 10B show in different states components of the add-on device of FIG. 9 mounted on a pen device.
Figure 10B:
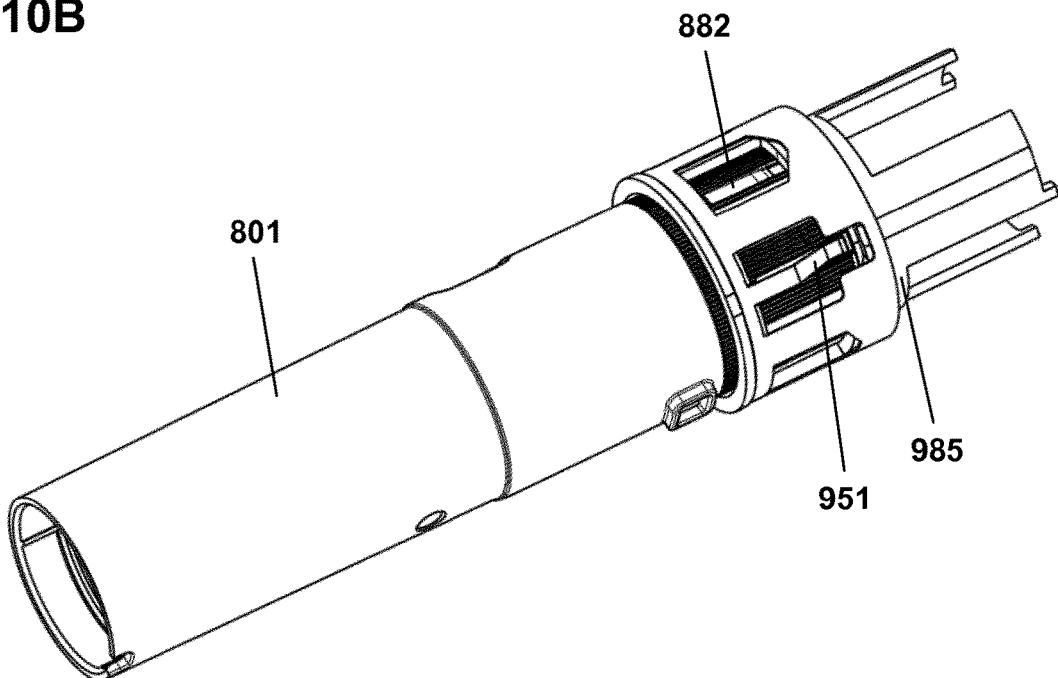

Turning to FIGS. 10A and 10B the proximal portion of a slightly modified pen drug delivery device 800 is shown in combination with the parts of the add-on device inner assembly providing rotational engagement between the add-on device and the pen dose setting member.

More specifically, the pen housing 801 generally corresponds to the embodiment of FIG. 6, however, instead of a slightly tapered housing the proximal coupling portion 802 of the housing including the window 809 has a "true" cylindrical form adapted to be received in the cylindrical bore of the add-on device. Alternatively, both structures may have a light taper. Further, the coupling means is in the form of a single locking protuberance 805 adapted to cooperate with the catch member 905 for easy axial mounting. Also shown is the dose setting member 880 having a generally cylindrical outer surface 881 (i.e. the dose setting member may be slightly tapered) which in the shown embodiment is textured by comprising a plurality of axially oriented fine grooves to improve finger grip during dose setting, as well as a number of axially oriented drive grooves 882 corresponding to the embodiment of FIG. 6.

As described above with reference to FIGS. 9A and 9B the inner assembly comprises a housing member 981 with a distal skirt portion 987 having a number of openings 989, as well as a cylindrical locking member 950 mounted thereon, the locking member comprising a number of flexible dial locking arms 951 and a number of flexible mounting arms (the latter not being shown in FIGS. 10A and 10B).

In FIG. 10A the inner housing 981 is shown in its axially mounted position (as determined by non-shown parts of the add-on device). Whereas the outer add-on housing 901 is mounted in a rotationally pre-determined position, this is not the case for the inner housing assembly which in an unmounted state is allowed to freely rotate relative to the outer housing, this providing that the inner housing and thus the locking arms 951 are mounted in a "random" rotational position such that the locking arms are not rotationally in register with the dose setting member drive grooves 882. Additionally, although the dose setting member 880 has an initial "parked" rotational "zero" position corresponding to no dose having been set, it may have been set in a random position. Additionally, even when parked in the zero position slack in the dose setting mechanism may result in slight variations in the rotational position of the dose setting member drive grooves.

Thus, when the add-on device is mounted on the pen device the flexible dial locking arms 951 may be out of rotational register with the dose setting member drive grooves 882. However, due to the dial locking arms being flexible they will be moved outwards by the dose setting member and axially slide on the outer circumference of the dose setting member in parallel with the drive grooves, this as shown in FIG. 10A. As the resistance provided by the flexible locking arms is small the user will in most cases not notice what has happened during mounting of the add-on device and will not be aware of the fact that the add-on device has not yet rotationally engaged the pen device dose setting member. In the shown embodiment the free end of the locking arms 951 are oriented proximally, however, alternatively they may be oriented distally with the free end of the locking arms and the proximal edge of the pen device dose setting member 880 configured to move the locking arms outwards during mounting of the add-on device.

Subsequently, when the user desires to set a dose, the user will start rotate the add-on device dose setting member 911 and thereby the inner housing with the locking arms 951 which then will be rotated into register with the dose setting member drive grooves 882 and thus be allowed to flex inwardly to rotationally engage the drive grooves, this as shown in FIG. 10B. To assure that the locking arms will easily engage the drive grooves they are formed slightly narrower than the drive grooves. Further movement of the add-on device dose setting member 911 will then cause the pen device dose setting member to rotate correspondingly, this allowing the user to set and adjust a dose as normally. Indeed, in a number of cases the locking arms will be moved directly into the drive grooves.

The number and the mechanical properties of the locking arms 951 should be dimensioned to allow for safe and robust operation of the add-on device. To assure this the combined assembly, i.e. the pen device and the add-on device may comprise an over-torque mechanism in case the user tries to dial below zero or above the maximum settable dose amount. For the add-on device an over-torque mechanism may be incorporated in the spline engagement between inner housing assembly and the add-on dose setting member, however, in most cases such a mechanism for the add-on device can be dispensed with, as pen devices in general will be provided with an over-torque protection mechanism, e.g. as know from the FlexTouch® drug delivery pen. Indeed, the locking arms 951 and the dose setting member drive grooves 882 should be designed and dimensioned to withstand torque above the limit for the pen device over-torque mechanism.

Figure 11A:
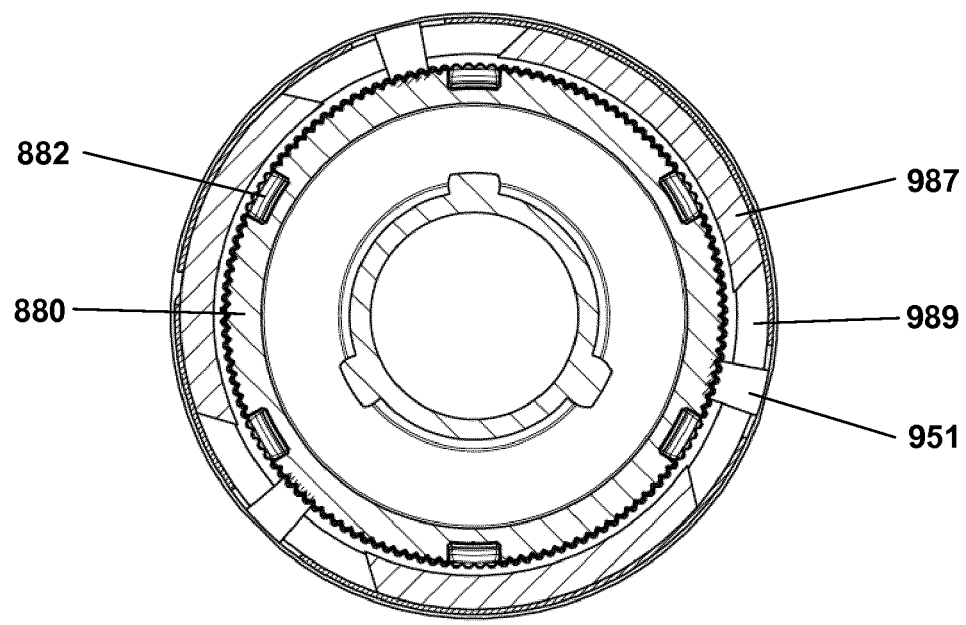
FIGS. 11A and 11B show cross-sectional views of the devices shown in FIGS. 10A and 10B, FIGS. 12A and 12B show in partial cut-away views the third embodiment in assembled state.
Figure 11B:
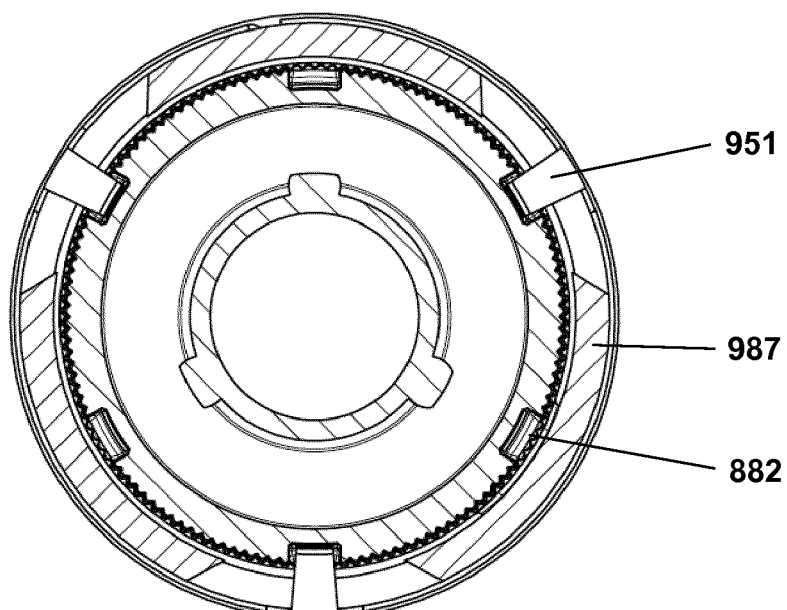

FIGS. 11A and 11B shows in cross-sectional views when the locking arms 951 have engaged the outer circumference of the pen device dose setting member 880 respectively have engaged the pen device dose setting member drive grooves 882.

Figure 12A:
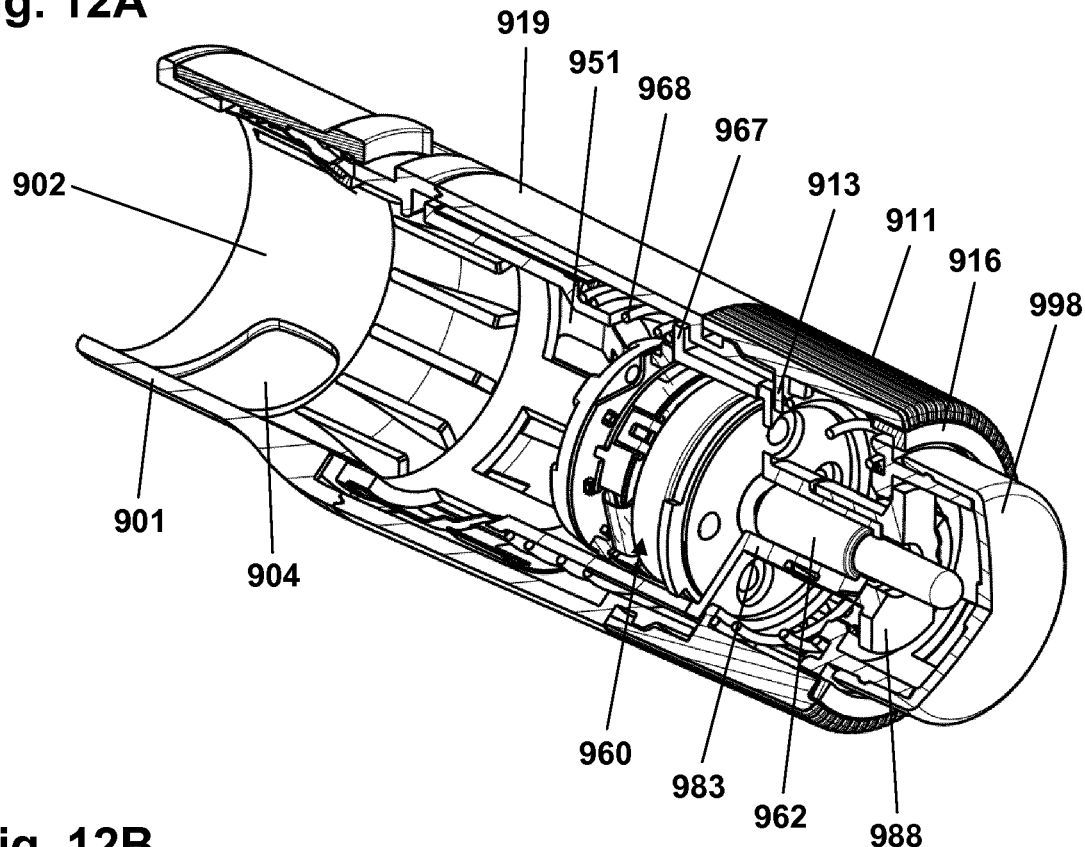
Figure 12B:
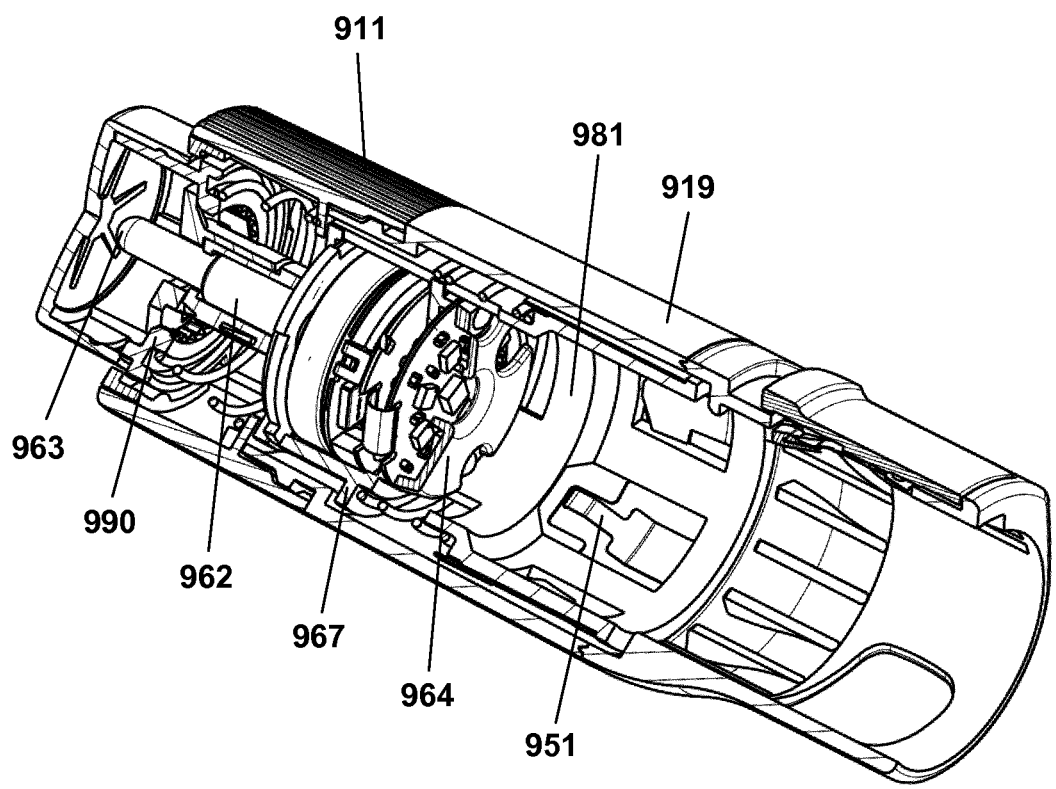

Turning to FIGS. 12A and 12B the components of FIG. 9A are shown in an assembled state corresponding to an initial non-mounted and non-actuated state.

More specifically, FIG. 12A shows the sensor module 960 arranged inside the inner assembly and being biased towards its proximal-most position by the sensor spring 968 acting between the inner housing spring support 984 and the sensor housing distal guide flanges 967. A dial locking arm 951 can be seen protruding into the interior of the inner housing skirt portion 987. The release body member 990 is biased towards its proximal-most position by the release member return spring 918 acting between the dose setting member inner flange 912 and the ring portion 994 of the release body member. The actuation rod 962 is arranged inside the inner housing tube portion 983 and axially held in place by the flange member 988, an axial gap being formed between the actuation rod proximal end 963 and the distal surface of the cap member 998. The inner housing and the release member assembly are rotationally locked to each other via the splined engagement between the tube portion 983 and the release body member 990 (cannot be seen in FIG. 12A).

With reference to FIGS. 13A-13F different operational states of the third exemplary embodiment of an add-on dose logging device 900 in combination with a pen-formed drug delivery device 800 will be described. The shown pen device is in the form of a FlexTouch® prefilled drug delivery device from Novo Nordisk A/S.

FIG. 13A shows the add-on dose logging device 900 prior to being mounted on the pen-formed drug delivery device 800. As described above the drug delivery device comprises a proximal coupling portion 802 having a "true" cylindrical form adapted to be received in the cylindrical bore of the add-on device, a window 809, a locking protuberance 805 adapted to cooperate with the add-on device catch member 905, a dose setting member 880 having a generally cylindrical outer surface 881 with a number of axially oriented drive grooves 882, and a proximally arranged release member 890. The add-on device 900 comprises a cylindrical bore 902 adapted to receive the cylindrical coupling portion 802 of the pen device, a catch member 905 adapted to engage locking protuberance 805, and a window opening 904 arranged to be mounted in register with the pen device window 809, a dose setting member 911 and a dose release member 998. Projecting into the bore 902 a dial locking arm 951 can be seen. Corresponding to FIG. 12A the add-on device is in its initial non-mounted and non-actuated state.

Figure 13B:
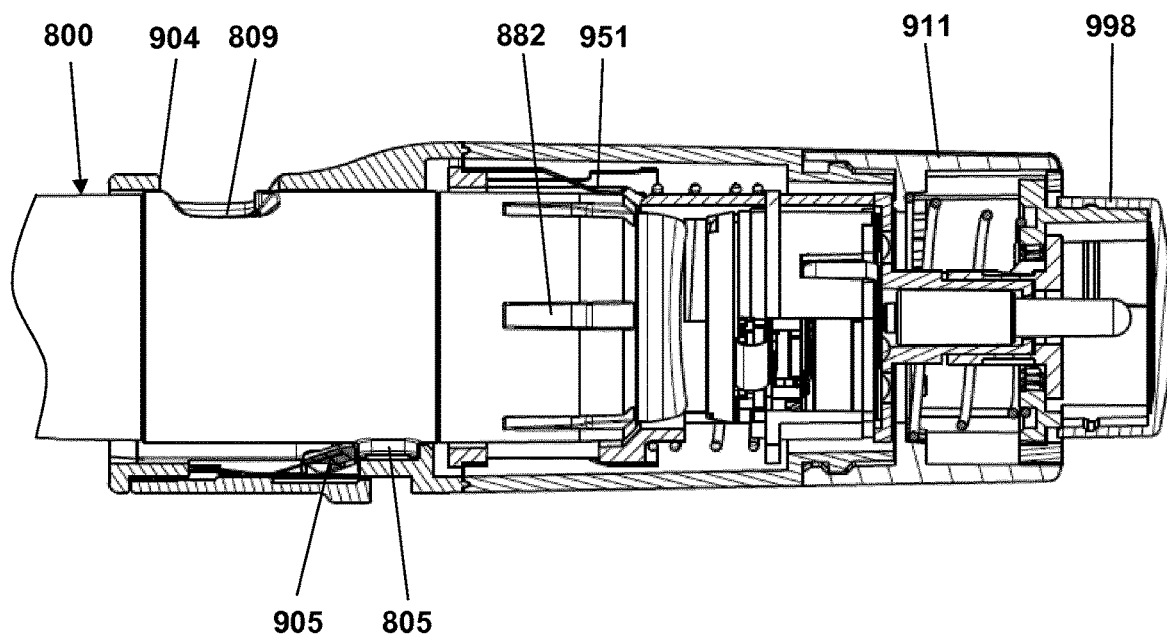

In FIG. 13B the add-on device 900 has been mounted on the pen device 800, with the catch member 905 seated distally of the locking protuberance 805 and the two windows 904, 809 in alignment. In the shown embodiment both the catch member 905 and the locking protuberance 805 are designed to provide a form-fitting engagement not relying on deformable or flexible structures. Due to tolerances for the different components this will in practise provided a coupling having a slight amount of slack. To minimize such a slack the locking/mounting arrangement may be provided with gripping structures, e.g. elastic structures, allowing the add-on device to be mounted on the pen device without slack. Corresponding to the situation shown in FIG. 10A the dial locking arms 951 have not yet engaged the drive grooves 882.

Figure 13C:
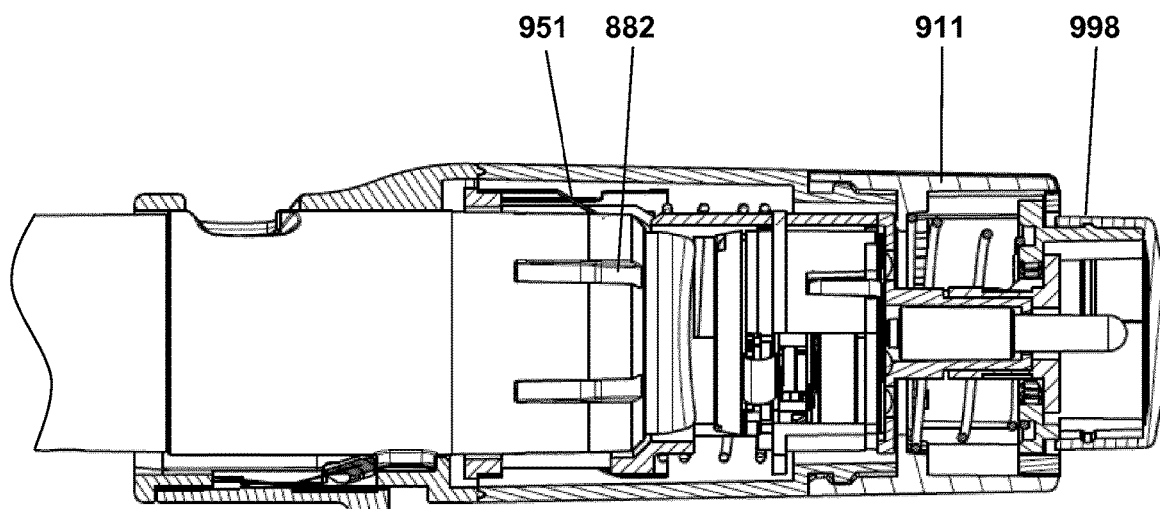

In FIG. 13C the add-on dose setting member 911 and thereby the inner assembly has been rotated, the dial locking arms 951 have engaged the drive grooves 882, and a dose has been set.

Figure 13D:
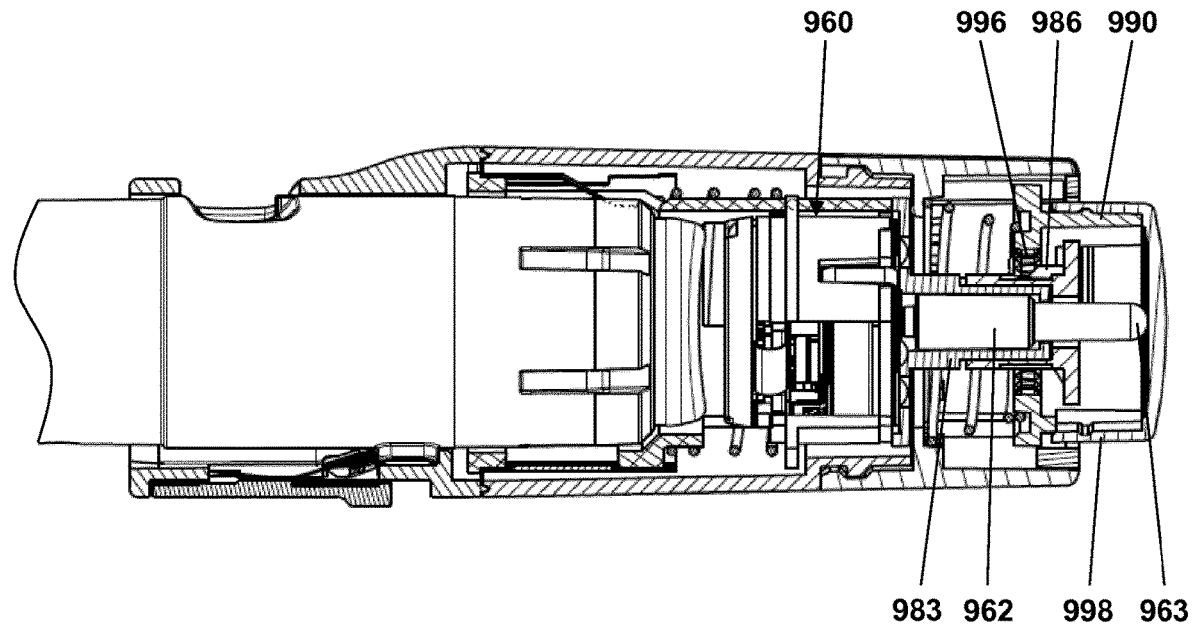

In FIG. 13D the add-on dose release member 998 has been partly actuated to just engage the actuation rod rounded proximal end 963, in which state the inner circumferential array of axially oriented splines 996 on the release body member 990 has disengaged the locking splines 986 on the tube portion 983, this rotationally decoupling the dose setting member 911 from the inner assembly and thus the sensor module 960. Further distal movement of the add-on dose release member will 998 start move the actuation rod 962 distally which initially will result in the proximally facing centrally arranged actuation switch 966 (see FIG. 9) being actuated by the actuation rod, this turning the sensor module into its operational state.

Figure 13E:
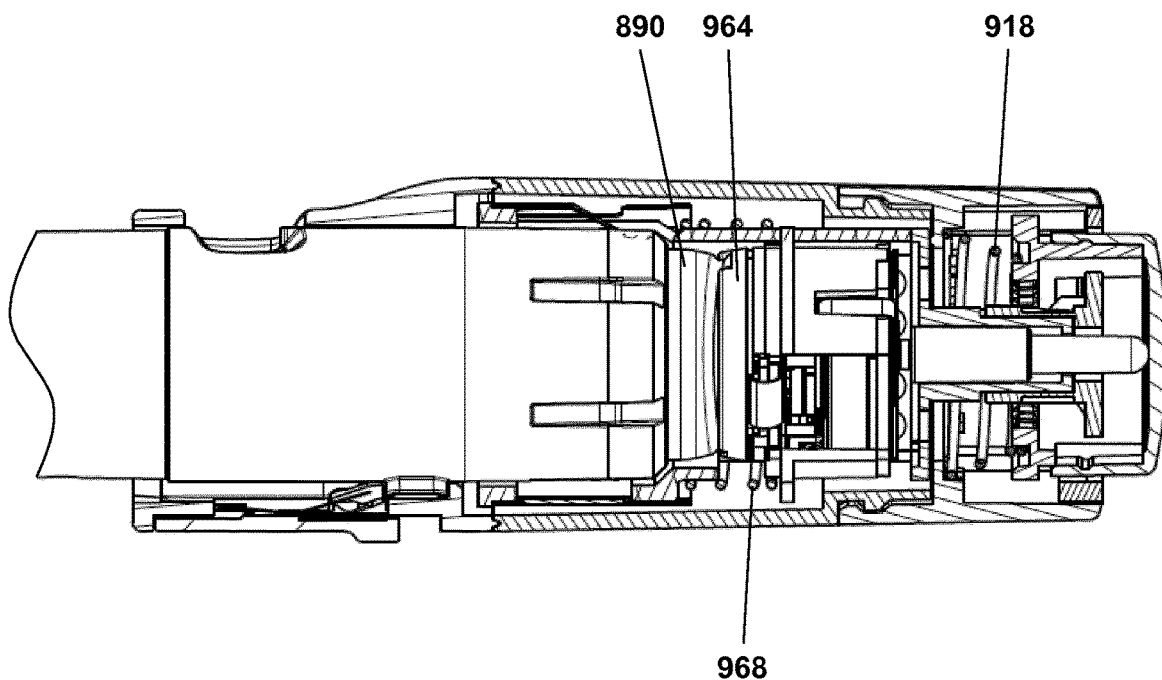

In FIG. 13E the add-on dose release member 998 has been further actuated to just move the sensor module spacer cap 964 into engagement with the pen device release member 890.

Figure 13F:
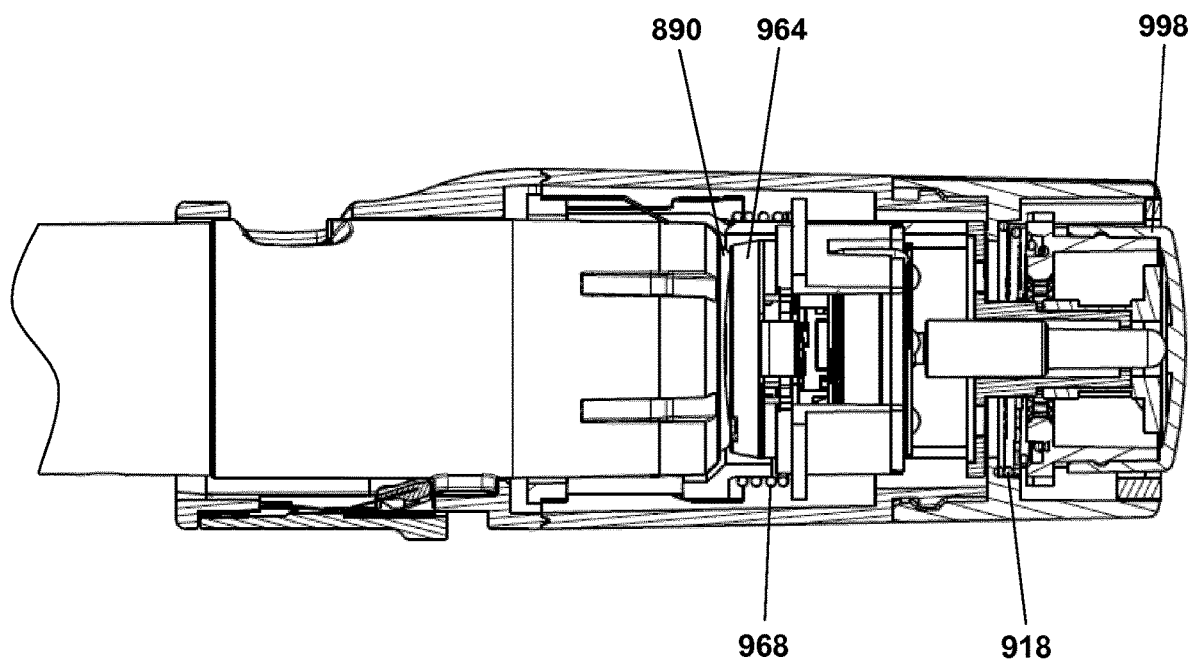

In FIG. 13F the add-on dose release member 998 has been fully actuated and the sensor module and thereby the pen device release member 890 have been moved to their distal-most operational positions, this releasing the expelling mechanism whereby the set dose of drug is expelled through a hollow needle mounted on the drug-filled cartridge. Determination of the expelled dose size may take place as described above with reference to FIGS. 8A-8D. When the set dose has been expelled the user may release pressure on the add-on dose release member 998 and the components will return to their initial axial positions due to the return springs 968, 918.

Turning to FIGS. 23A-26B a fourth exemplary embodiment of an add-on dose logging device 1200 adapted to be mounted on the pen-formed drug delivery device 800 will be described, the add-on device 1200 comprising an alternative mounting interface.

The add-on dose logging device 1200 essentially corresponds to the add-on dose logging device 600 described with reference to FIGS. 6-8 and thus comprises an outer assembly releaseably attachable to a drug delivery device housing, an inner assembly with a sensor module as well as a release member assembly.

More specifically, the outer assembly comprises a distal coupling portion with a generally cylindrical outer add-on housing 1201 defining a general axis for the add-on device, the coupling portion having a cavity in the form of a generally cylindrical bore adapted to receive a corresponding generally cylindrical proximal coupling portion of the drug delivery pen 800 and being adapted to be mounted axially and rotationally locked on the drug delivery housing by means of a number of gripping structures 1215 adapted to engage and grip the proximal cylindrical coupling portion 802 of the pen housing. The add-on device further comprises a proximal dose setting member 1205 mounted freely rotatable on the coupling portion and which like in the embodiment of FIG. 6 can be coupled to the pen dose setting member 880 such that rotational movement of the add-on dose setting member 1205 in either direction is transferred to the pen dose setting member. The add-on device further comprises a dose release member 1290 which during dose setting rotates with the dose setting member. As in the embodiment of FIG. 6 the inner and outer assemblies are rotationally locked to each other during dose setting, but rotationally de-coupled from each other during dose expelling.

A generally ring-formed gripping member 1210 is arranged in the receiving bore, the gripping member comprising a plurality of flexible distal gripping arms 1215 having a radially open state allowing the drug delivery device housing proximal portion to be received (se FIG. 23A), and a radially closed state allowing the gripping arms to engage the drug delivery device housing proximal portion 802 (see FIG. 23B) when the add-on housing 1201 is moved distally relative to the gripping arms as will be described in greater detail below. The add-on device 1200 further comprises a drive member 1220 adapted to receive the dose setting member 880 and being releasably attached thereto in a rotationally non-moveable position.

Figure 23A:
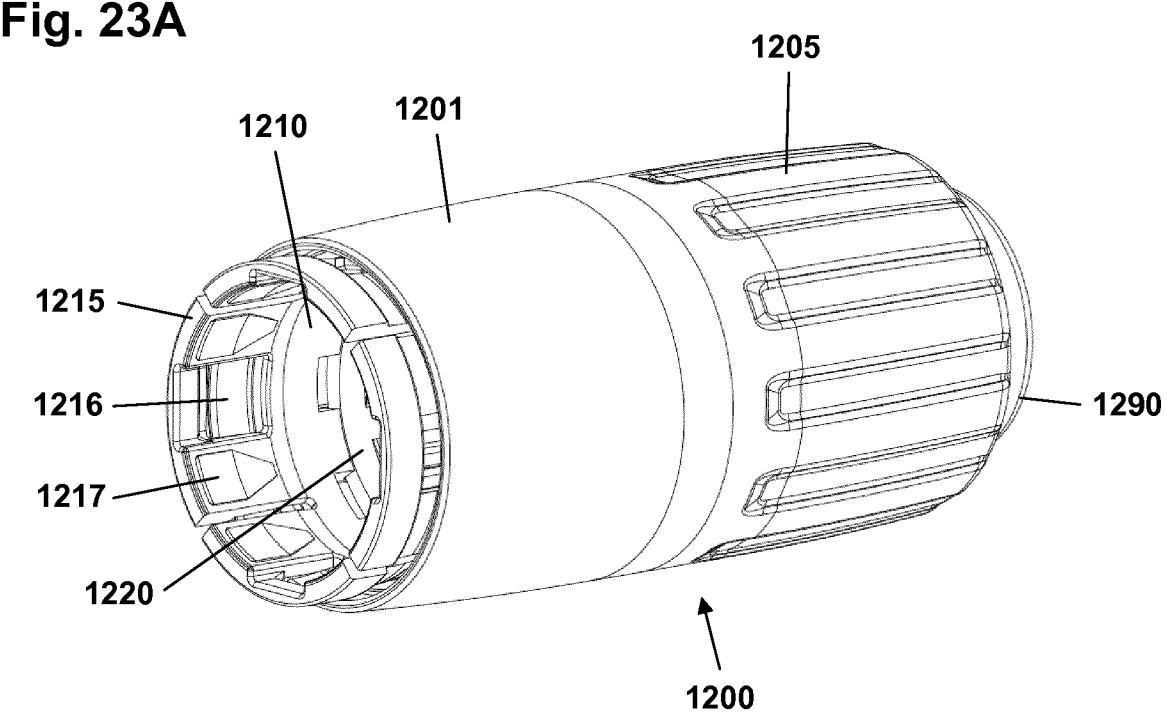
FIGS. 23A and 23B show in different operational states a fourth embodiment of an add-on device.

In the shown embodiment four circumferentially curved gripping arms 1215 each spanning close to 90 degrees form a circumferential gripping array. Each curved gripping arm comprises a central cut-out portion 1216 adapted to receive and glide over the housing protuberance 805, this allowing the add-on device to be mounted in four different rotational positions in order to allow for ease of mounting. Indeed, this feature is only relevant for a pen device comprising such a protuberance. On each side of the central cut-out an elastomeric pad area 1217 is provided, e.g. by 2K moulding, and adapted to frictionally engage the pen housing when the gripping arms are actuated to their gripping state shown in FIG. 23B. As appears, the length of the coupling portion of the fourth embodiment is somewhat shorter than in the third embodiment and thus does not require an opening for the pen housing window 809. Although the shown embodiment 1200 of FIG. 23A is specifically adapted for mounting on pen device 800 of FIG. 13A, it does not require a pen coupling portion being strictly cylindrical and could thus also be mounted on a non-modified pen housing of the type shown in e.g. FIG. 1A, the gripping arms and the size of the elastomeric pads providing a secure axial grip also preventing tilting to a high degree.

Figure 24:
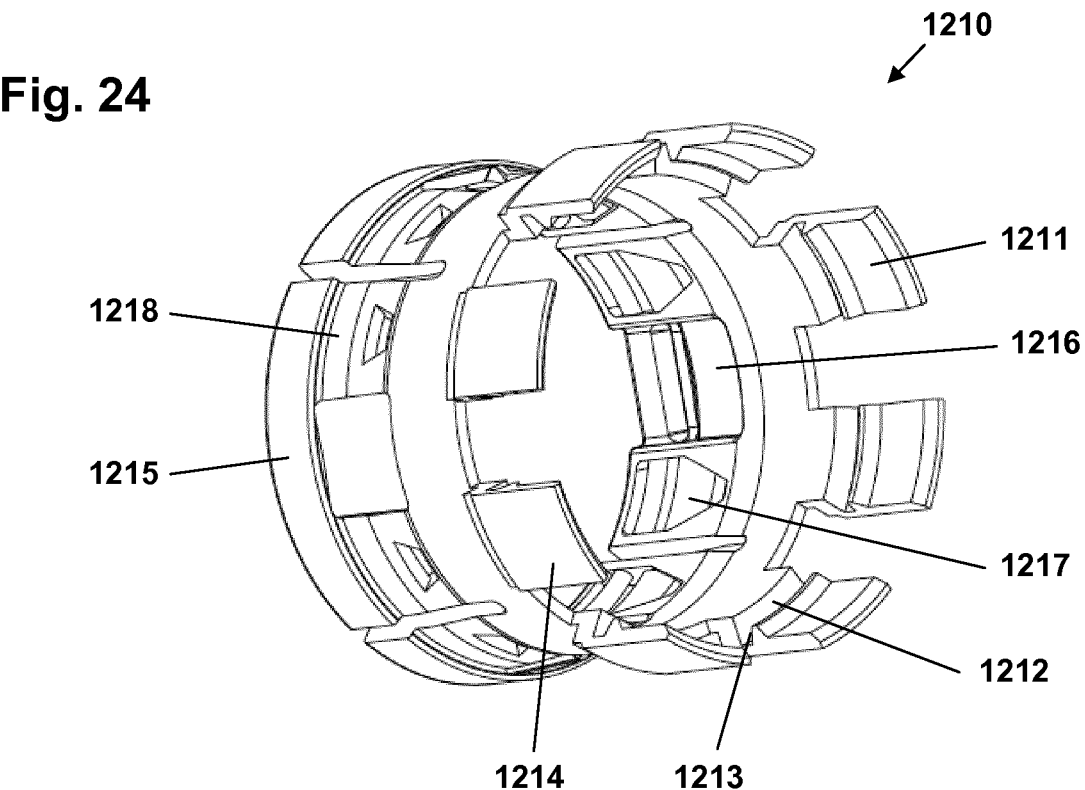
FIG. 24 shows a gripping member forming part of the fourth embodiment.
Figure 25:
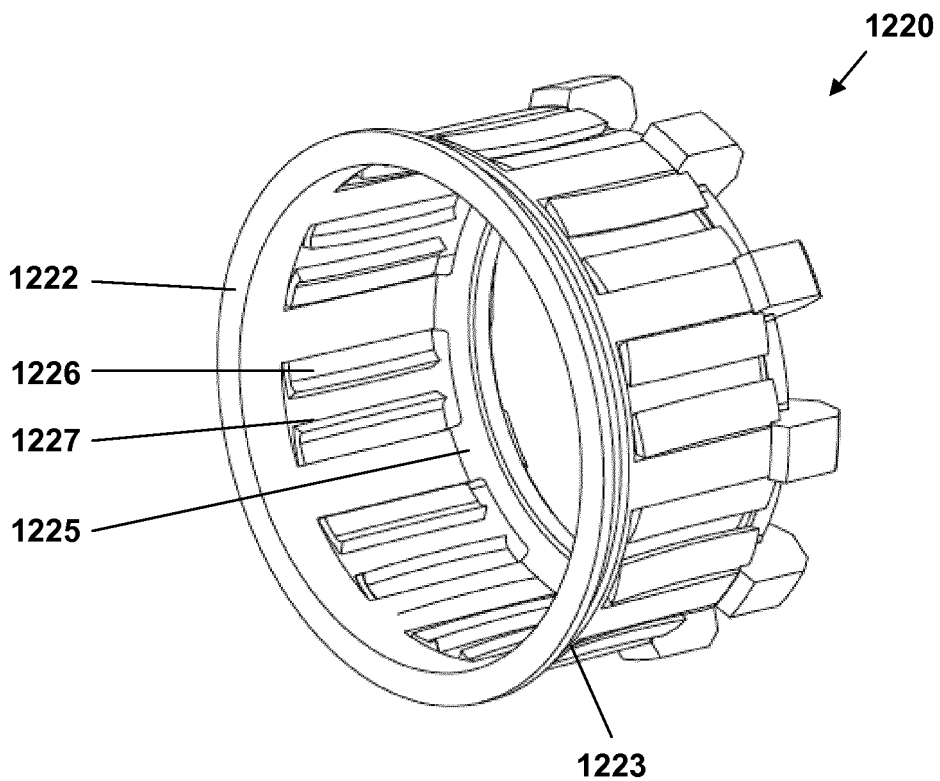
FIG. 25 shows a drive member forming part of the fourth embodiment.

Turning to FIGS. 24 and 25 the gripping member 1210 respectively the driving member 1220 is shown. The generally cylindrical gripping member 1210 comprises the above-described four distally extending gripping arms 1215 each comprising a cut-out portion 1216 and a pair of relatively soft elastomeric pad areas 1217. On the outer surface the gripping arms comprise circumferentially arranged locking grooves 1218 adapted to be engaged by a corresponding circumferential locking ridge arranged distally on the add-on housing inner surface (see below). The gripping member further comprises a plurality of flexible proximally extending coupling flanges 1211 with an outer surface 1214, each flange comprising a proximally facing coupling surface 1212 and a coupling ridge comprising a distally faced inclined coupling surface 1213.

The generally cylindrical drive member 1220 comprises a distal ring portion with a distally facing circumferential coupling surface 1222 adapted to engage the proximally facing coupling surfaces 1212 on the gripping member, as well as a proximally facing circumferential inclined coupling surface 1223 adapted to engage the distally facing inclined coupling surfaces 1213 on the gripping member. The drive member further comprises a proximal ring portion with an inner distally facing circumferential stop surface 1225 adapted to engage the proximally facing circumferential edge portion of dose setting member 880. Between the two ring portions the drive member is provided with a plurality of axially oriented inwards drive flanges 1226 having a sharp edge 1227 adapted to engage the axially oriented fine grooves on the pen dose setting member 880. Not shown a spring member is arranged to exert an axial distally directed biasing force, this ensuring that prior to mounting the gripping member is positioned in its distal-most position and thus open state.

As follows from the above, when the gripping member 1210 and the drive member 1220 are mounted in the add-on housing 1201, they are axially coupled to each to allow the drive member to "push" the gripping member in the distal direction, and allow the gripping member to "pull" the drive member in the distal direction.

Figure 23B:
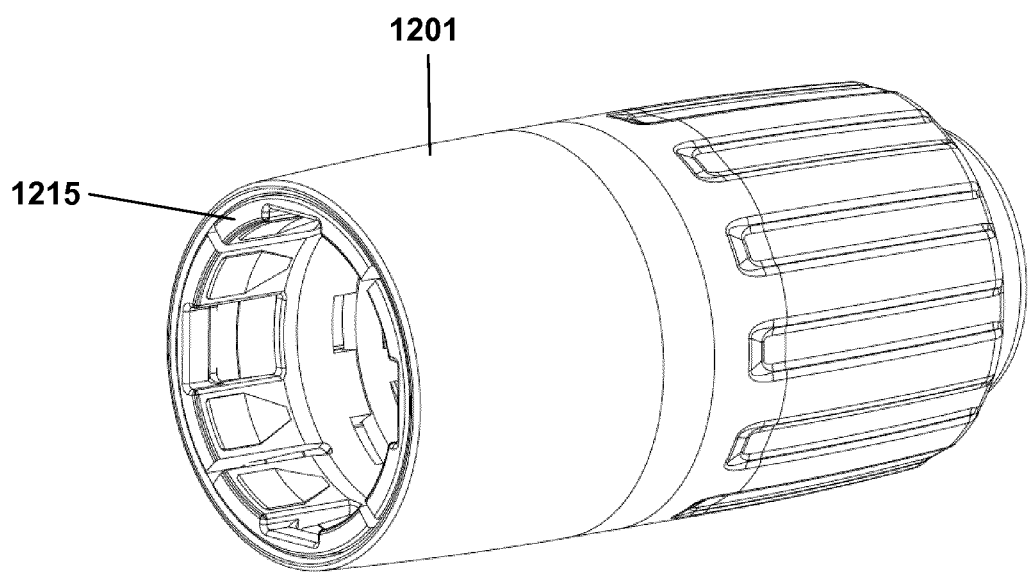
Figure 26A:
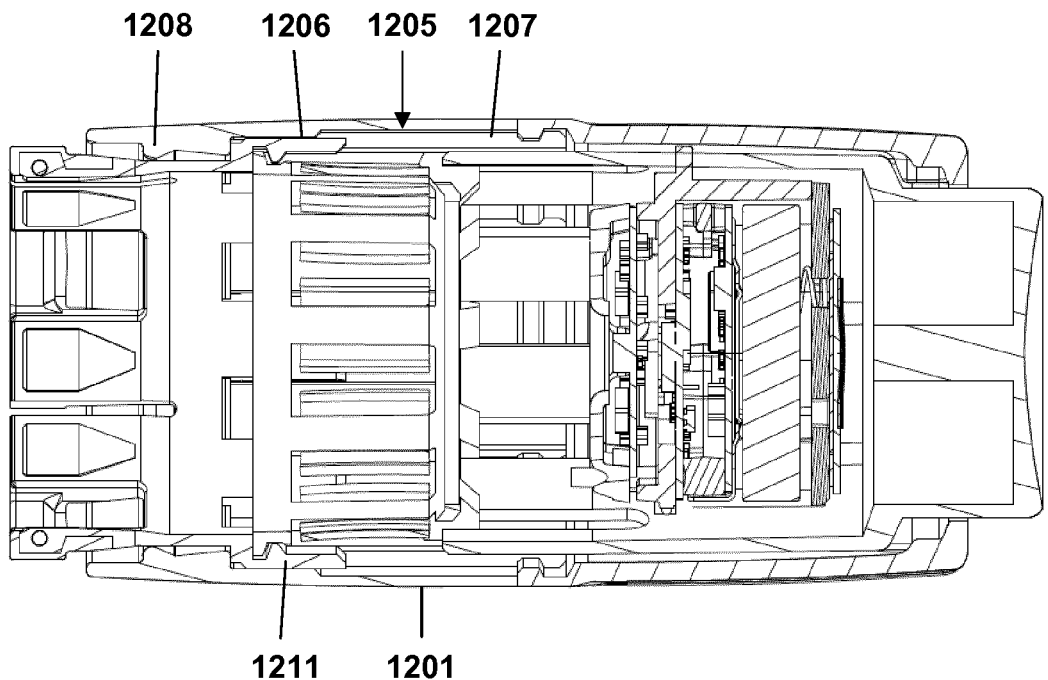
FIGS. 26A and 26B show in cross-section different operational states of the fourth embodiment of an add-on device.
Figure 26B:
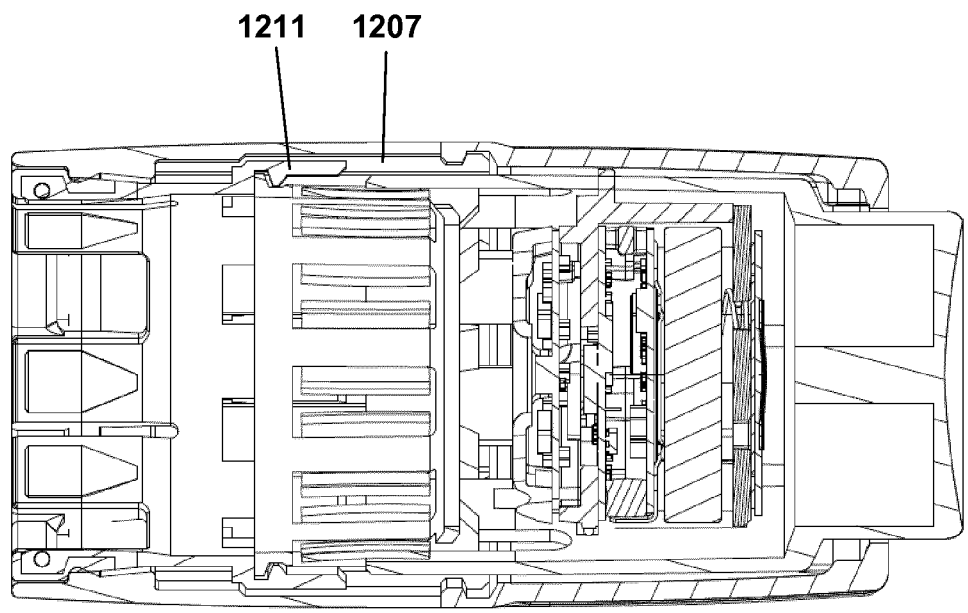

Turning to FIGS. 26A and 26B cross-sectional views of the add-on device of FIGS. 23A and 23B are shown in an open respectively closed state. In the following mainly the gripping member 1210, the drive member 1220 and the add-on housing 1201 and their functional relationship will be described, the remaining portion of the add-on device essentially corresponds to the add-on dose logging device 600 described with reference to FIGS. 6-8.

The generally cylindrical add-on housing 1201 comprises a plurality of axially oriented recesses 1205 adapted to receive the gripping member coupling flanges 1211. Each recess comprises a distal shallow portion 1206 and proximal deeper portion 1207. The housing further comprises a circumferential distal inner rounded locking ridge 1208 adapted to glide over the outer surface of the gripping arms 1215 and into snap locking engagement with the locking groove 1218 (not seen in FIGS. 26A and 26B).

In FIG. 26A the gripping member 1210 is positioned in its distal-most position corresponding to its open state allowing the gripping arms 1215 to flex radially outwards, the coupling flanges 1211 being positioned in the shallow distal portion of the coupling recesses, this preventing the coupling flanges to flex outwards. The locking ridge 1208 is designed to engage the proximal portion of the outer surface of the gripping arms 1215 in a snap action manner. In FIG. 26B the gripping member 1210 is positioned in its proximal-most position corresponding to its closed state with the gripping arms 1215 moved radially inwards, the coupling flanges 1211 being positioned in the deeper proximal portion 1207 of the coupling recesses (see below), this allowing the coupling flanges to flex outwards. The locking rib 1208 has engaged the locking grooves 1218 of the gripping arms 1215 thereby forcing the arms inwardly and thus, when mounted on a pen device, into gripping engagement with the pen housing.

When mounting the add-on device 1200 on a suitable pen device the user typically holds the add-on device in one hand and the pen device in the other hand and inserts the pen device proximal end into the receiving bore of the add-on device. To prevent the distally extending gripping arms to be prematurely pushed into the bore, an axial biasing force is exerted by the (not shown) spring acting on the drive member 1220, the drive member coupling surface 1222 axially pushing on the proximally facing coupling surfaces 1212 on the gripping member. The first interaction takes place when the drive flange edges 1227 axially engage the fine grooves on the pen dose setting member 880 until the dose setting member engages the gripping member stop surface 1225 in its fully seated position. As the user continuous to push the pen device and the add-on device towards each other, the add-device housing 1201 starts to move distally relative to the gripping member until the locking rib 1208 has seated in the gripping arm locking grooves 1218 thereby forcing the arms inwardly and thus snap into gripping engagement with the pen housing. As the locking rib glides over the gripping arm outer surfaces a distally directed force is exerted on the gripping member and correspondingly on the thereto coupled gripping member via the inclined coupling surfaces 1213, 1223. As the coupling flanges 1211 are seated in the shallow portion 1206 of the coupling recesses 1205, the inclined surfaces are prevented from being forced radially apart from each other. Consequently, a distally directed force is exerted on the pen dose setting member 880 forcing it against the pen housing, this being an undesirable condition causing friction to rotation of the dose setting member relative to the pen housing. Addressing this issue, just prior to the locking rib 1208 engaging the locking grooves 1218 of the gripping arms 1215, thereby forcing the arms inwardly, the coupling flanges 1211 enter the deeper portion 1207 of the coupling recesses, this allowing the flanges with the inclined coupling surfaces 1213 to flex outwardly and thereby allowing the inclined surfaces to disengage, this releasing the pressure forcing the pen dose setting member 880 against the pen housing.

When the user desires to remove the add-on device from the pen device, the user simply pulls the two devices from each other, thereby reversing the above-described interactions allowing the snap lock to disengage.

Whereas the embodiment of FIGS. 23A-26B has been adapted specifically to allow mounting on the FIG. 13A pen device 800, with reference to FIG. 27 an alternative fifth embodiment of an add-on device 1300 will be described, the device being designed for mounting on a pen device not having a housing locking protuberance 805.

More specifically, instead of four gripping arms provided with elastomeric soft pads the add-on device 1300 is provided with an array of 12 gripping arms 1315 provided with spikes 1316, the spikes forming two circumferential arrays of spikes. The spikes are formed from a material somewhat harder than the material used for the pen housing, this providing that the spikes with the add-on device 1300 mounted on a pen will "bite" into the surface of the pen housing, this ensuring a firm grip. The pen device housing may typically be made from a relatively soft polymer such as polypropylene, for which spikes made from e.g. nylon would be a good match. Correspondingly, the gripping may be fully or partly moulded in nylon. Alternatively, the spikes could be made from metal. As the add-on device 1300 is primarily intended to be used in combination with prefilled disposable pen devices, slight impressions made by the spikes would not be an issue.

Figure 27:
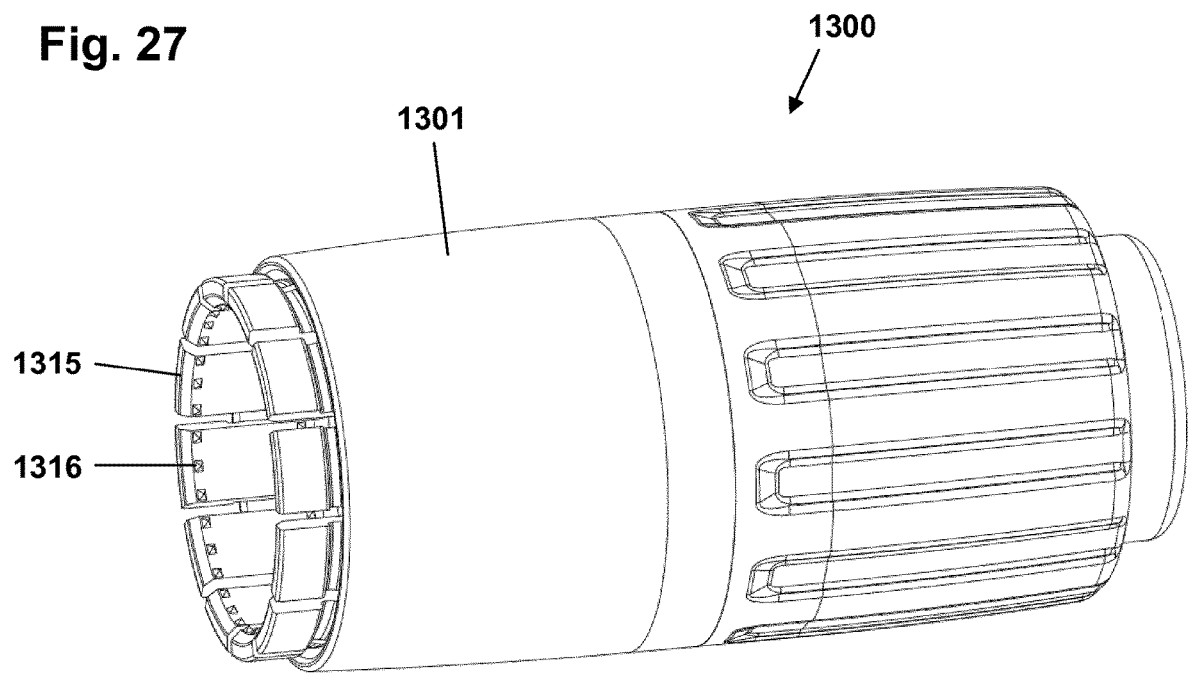
FIG. 27 shows a fifth embodiment of an add-on device.

Apart from the alternative configuration of the gripping arms 1315, the add-on device 1300 of FIG. 27 may be designed in the same way as the above-described add-on device of FIG. 23A.

In addition or as an alternative to the above-described snap lock, the add-on device may be provided with a mounting locking mechanism which may have to be positively operated by the user to lock and/or unlock the add-on device to the pen body, e.g. of the type as described with reference to the FIG. 9 embodiment.

In addition or as an alternative to the above-described gripping arrangement based on friction, the assembly may comprise add-on gripping means adapted to engage corresponding engaging structures on the drug delivery device housing proximal portion, e.g. in the form of a circumferential groove.

Although the mounting interfaces described with reference to the embodiments of FIGS. 23A-27 are described in combination with a specific type of sensor arrangements, the described mounting interface concept may be used with corresponding effect in alternative types of add-on devices relying on other sensor concepts for determining the amount of an expelled amount of drug.

For example, the pen indicator may be a component in a sound or vibration generating mechanism generating a sound or vibration pattern, e.g. a number of click sounds, during drug expelling, the generated sound or vibration pattern being indicative of the size of the expelled dose amount. Correspondingly, the add-on sensor means may be in the form of a microphone. The indicator may be a drum with indicia rotating during drug expelling, e.g. a scale drum with dose numerals, the amount of rotation being indicative of the size of the expelled dose amount. Correspondingly, the add-on sensor means may be in the form of a camera in combination with electronic circuitry for OCR analysis. Alternatively, the indicator may be adapted to move during dose setting, the amount of movement being indicative of the size of the set dose amount and thus the assumed amount of subsequently expelled drug. Correspondingly, the add-on sensor means may be in the form of a rotary encoder coupled to the dose setting member via the gripping member.

Having described the mechanical concept and working principle of the add-on dose logging devices of FIGS. 5, 7A and 12A, the sensor and tracer system per se will be described in greater detail. Basically, the sensor and tracer system comprises a moving magnetic tracer component and a sensor system comprising one or magnetometers, e.g. 3D compass sensors.

Figure 14:
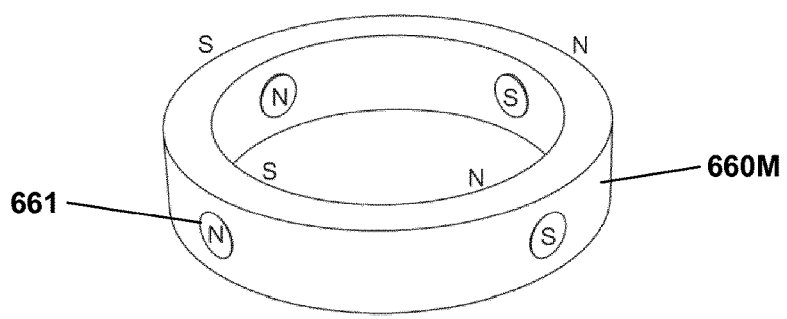
FIG. 14 shows individual dipole magnets arranged equidistantly in a ring-formed tracer component.

In an exemplary embodiment the magnetic tracer component is in the form of a multi-pole magnet having four poles, i.e. a quadrupole magnet. In FIG. 14 four dipole standard magnets 661 have been arranged equidistantly in a ring-formed tracer component 660M, the four separate dipole magnets providing a combined quadrupole magnet with the four poles offset by 90 degrees. Indeed, each of the dipole magnets are formed by a very large number of individual magnetic particles oriented in the same direction. The individual magnets may be arranged in the same plane or may be axially offset from each other.

Figure 15A:
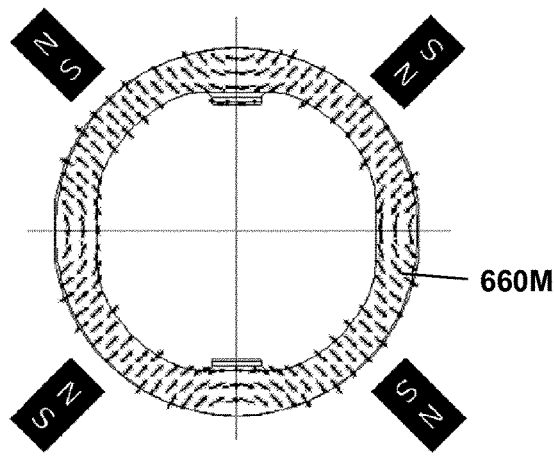
FIG. 15A shows a tracer component manufactured from a magnetisable material in combination arranged between individual magnets.
Figure 15B:
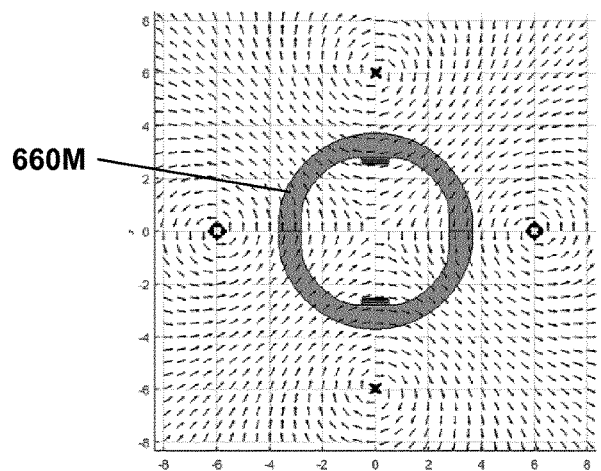
FIG. 15B shows a tracer component manufactured from a magnetisable material arranged in a multipolar electromagnetic field.

Alternatively, a multi-pole magnet 660M can be created by magnetization of a magnetisable material either by use of individual powerful magnets as shown in FIG. 15A, or through use of electromagnetic fields as shown in FIG. 15B.

Figure 16:
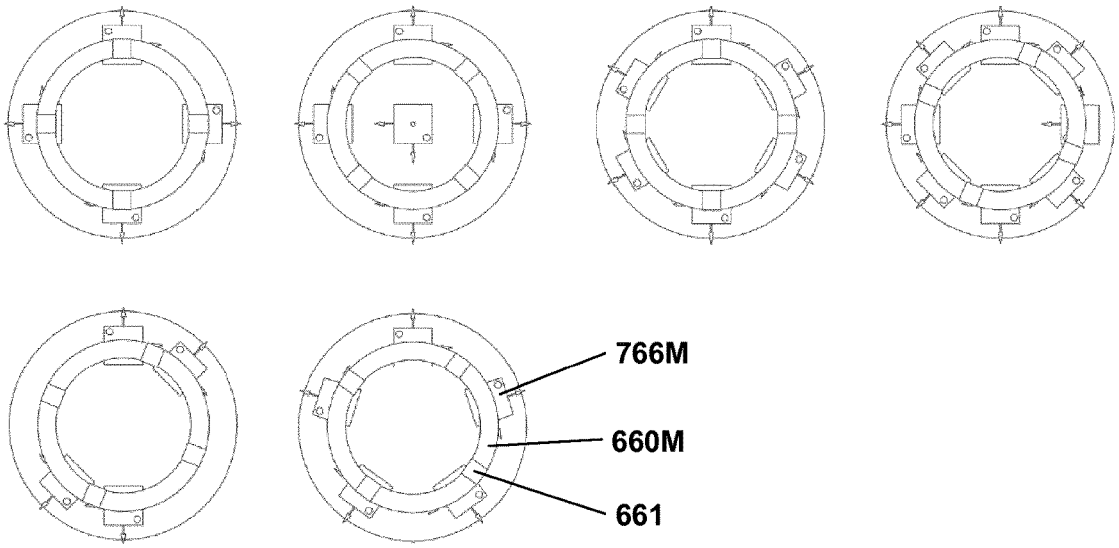
FIG. 16 shows different embodiments of a sensor system comprising magnetometers arranged relative to a tracer component.

A given sensor system may be using e.g. 4, 5, 6 or 8 magnetometers 766M arranged relative to a tracer component 660M as illustrated in FIG. 16. The sensors may be arranged in the same plane, e.g. as shown in FIG. 7B, or they may be axially offset from each other. The more sensors, the smaller spacing between the sensors and thus more data with a better signal-to-noise ratio can be gathered. However, the more sensors, the more data processing is required and the more power is consumed.

In some cases, not only disturbances from external fields need to be handled. The torque-providing spring for driving the dose expelling motor in the disposable device as described above may be magnetized when subjected to an external magnetic field and thus provide an internal disturbing magnetic field.

Where external disturbances may be cancelled out to a large extent by signal processing algorithms, because they influence all the sensors more or less equally and in the same direction, a magnetized torque spring will influence the sensors much like the tracer magnet and therefore be more likely to offset the measurements and cause errors.

Figure 17A:
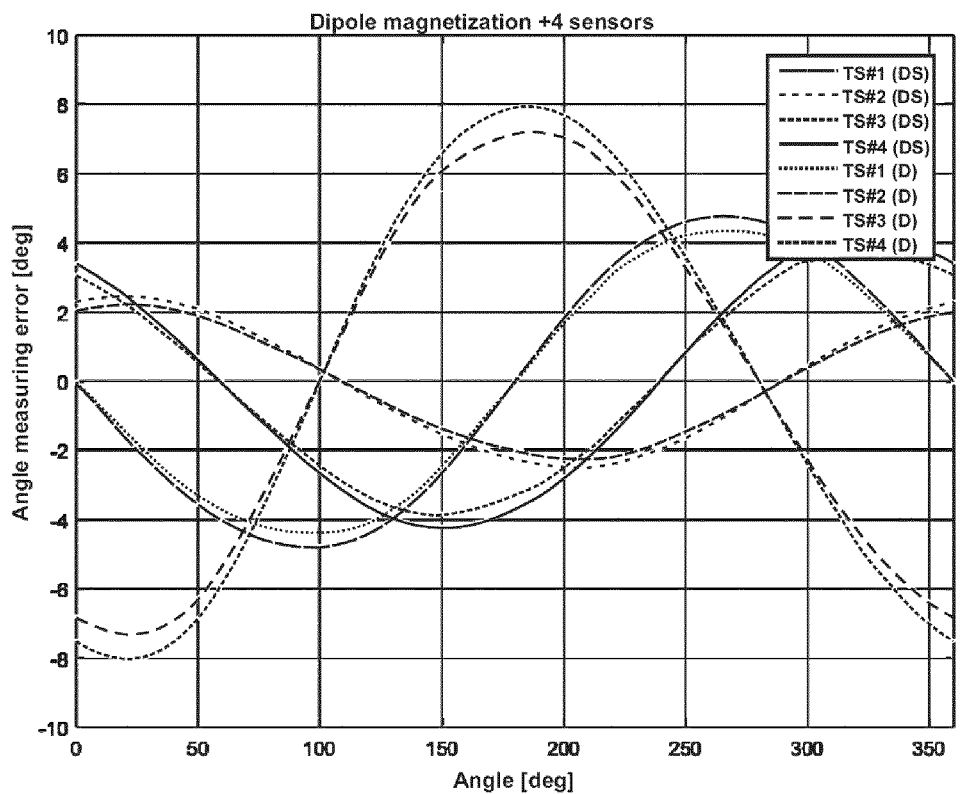
FIG. 17A shows angle measurements for a dipole tracer magnet in combination with a first sensor set-up.
Figure 17B:
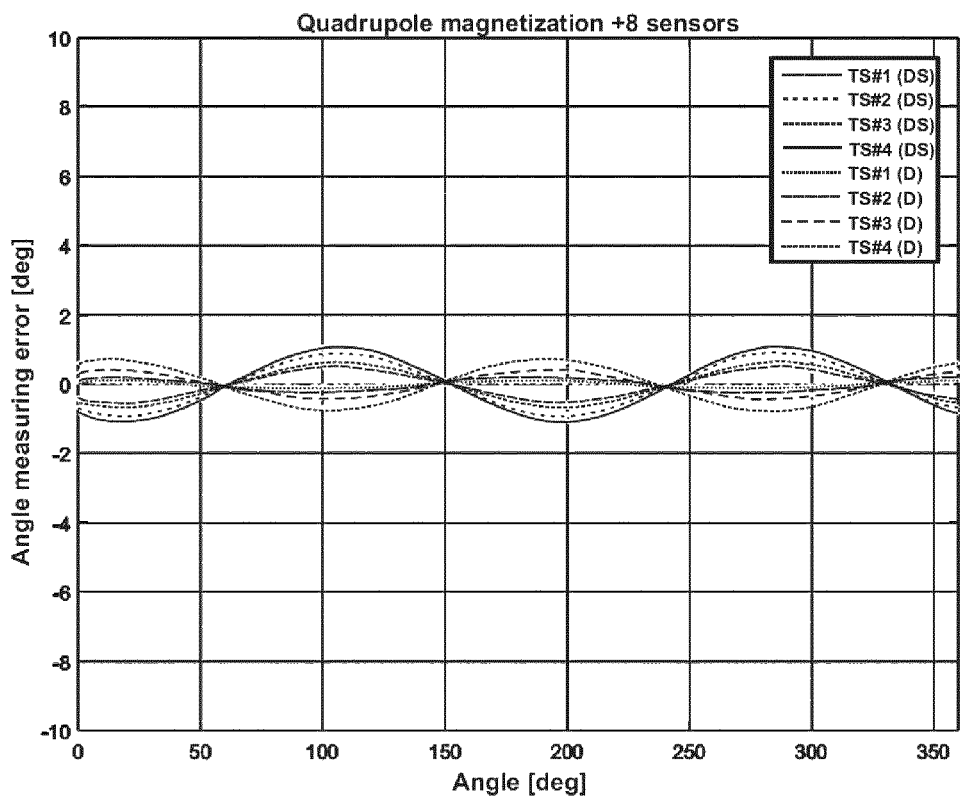
FIG. 17B shows angle measurements for a quadrupole tracer magnet in combination with a second sensor set-up.

However, as it can be seen from FIGS. 17A and 17B the use of a quadrupole tracer magnet instead of a dipole tracer magnet, significantly reduce the error in determining the position of the tracer magnet.

More specifically, FIGS. 17A and 17B show simulations of the influence of a magnetized torque spring at four different levels of magnetization (TS1-TS4) for both dose-setting (DS) and out-dosing (D). FIG. 17A illustrates the calculated angle measuring error (i.e. the difference between the calculated angle and the true angle) for a dipole tracer magnet in combination with a 4 sensors set-up, and FIG. 17B illustrates the calculated angle measuring error for a quadrupole tracer magnet in combination with an 8 sensors set-up. Due to the sensors being closer to the tracer magnet during out-dosing (see e.g. FIGS. 8A and 8C) the angle error is slightly smaller during out-dosing. This said, in the above-described embodiment sensor measurements take place only during out-dosing. For the quadrupole tracer magnet 8 sensors were used as the smaller circumferential spacing between the individual poles in the quadrupole tracer magnet provides a higher input rate to the sensor system which can be more precisely captured by 8 instead of 4 sensors, however, comparable results would be expected for a quadrupole tracer magnet in combination with a 4 sensors set-up. As appears, use of a quadrupole tracer magnet reduces the angle error from ca. 4-8 degrees to ca. 0.5-1 degrees, roughly a factor of 8.

In the shown FlexTouch® drug delivery device the reset tube 660 and thus the tracer magnet 660M rotates 7.5 degrees for each unit of insulin expelled. Thus, a possible angle error in the 4-8 degrees range may result in an incorrect determination of the expelled dose amount.

The quadrupole tracer magnet is thus not only reducing the systems sensitivity to disturbances from external fields, but also from internal fields. This is an important aspect of using a multipole tracer magnet, since traditional magnetic shielding of external sources by use of an iron-containing metallic sheet may be used to reduce the influence of external fields, but may not be possible to fit between the tracer magnet and an internal disturbing magnetic field. Further, incorporating a magnetic shield would take up space and introduce additional costs.

Alternatively, this may be mitigated by using a spring of a non-magnetisable material, however, current spring-driven pens on the market today comprise a magnetisable torque spring and replacement may not be feasible due to other requirements of the spring.

Having described the structural set-up for a sensor assembly incorporating a rotating quadrupole tracer magnet, in the following an exemplary method of determining actual movements for such an assembly will be described.

Figure 18:
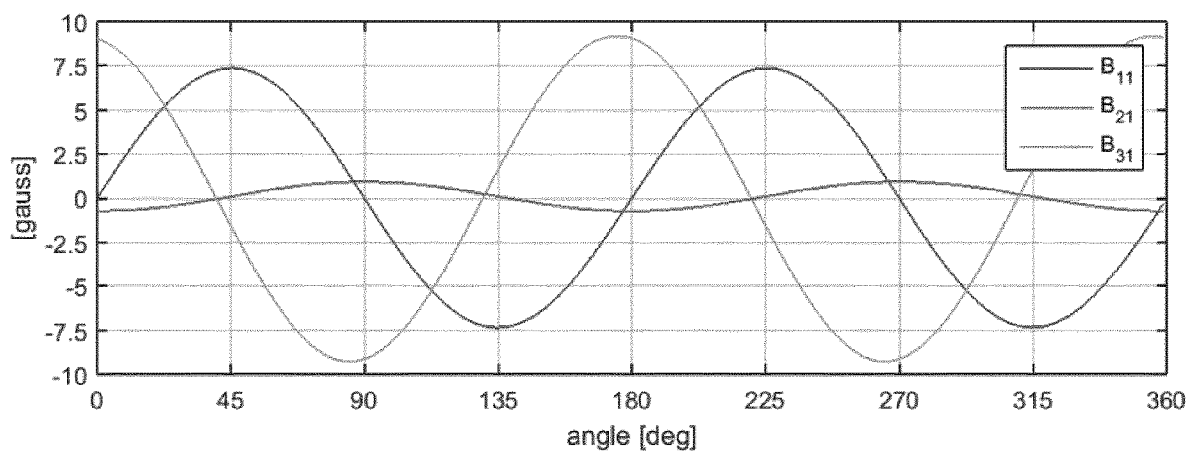
FIG. 18 shows signals from a quadrupole magnet over one full revolution of the magnet.

The signal from the quadrupole magnet is periodic with a period two over one full revolution of the magnet. This can be seen from FIG. 18 where the tangential, radial and axial field level is pictured.

Figure 19:
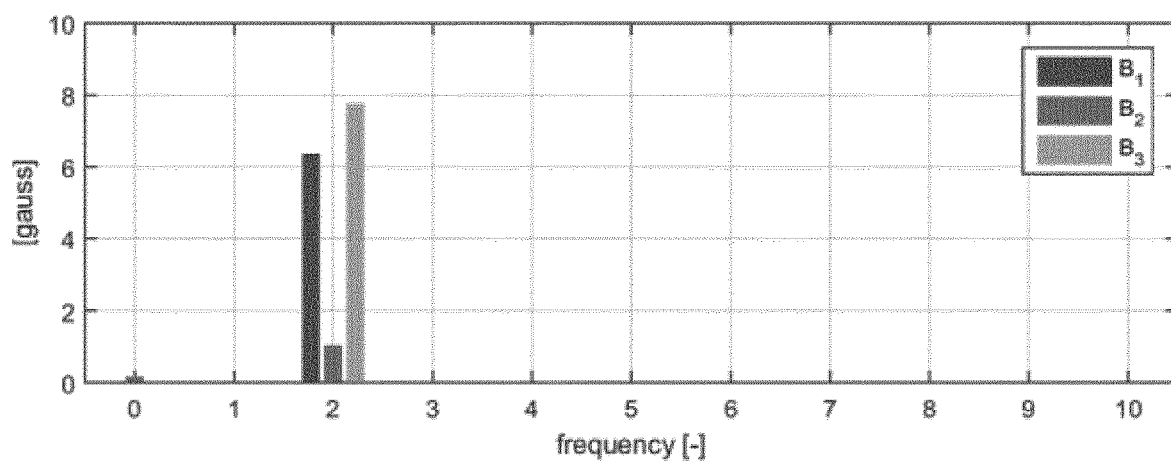
FIG. 19 shows a map of the frequency components of the signal from FIG. 18.

Mapping the frequency components of the signal, it is seen that all most the entire signal from the magnet fits into the frequency two signal, see FIG. 19.

Figure 20:
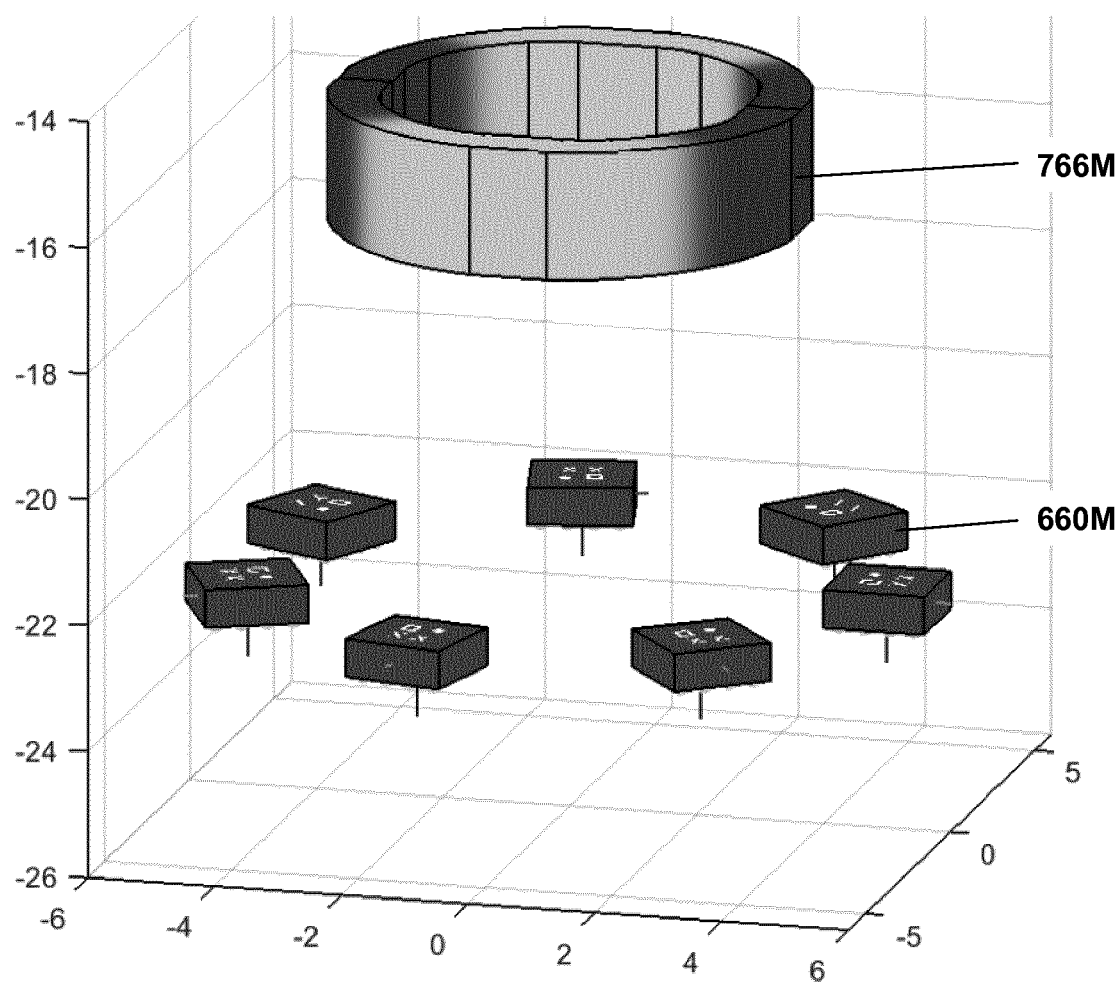
FIG. 20 shows an assembly of a quadrupole magnet and 7 magnetometers.

To determine a dose size utilizing at the quadrupole field, it is necessary to determine the static start and end angle of the quadrupole magnet. Since the magnet is static before and after the dose has been delivered, the field is sampled over space instead of sampled over time. In an exemplary embodiment a measurement system is configured with N=7 sensors with circular layout and equal spacing, see FIG. 20 showing sensor 766M placements relative to the quadrupole magnet 660M.

In order to determine the orientation or the magnet, a discrete Fourier transform (DFT) is computed on the field measured in the sensors $$\hat{B}_{jn} = \frac{2}{N}\sum_{k=1}^{N} B_{jk}\exp(-2\pi i k n/N).$$

Here $B_{jk}$ is the field in the j'th channel of the k'th sensor, j=1 is tangential field, j=2 is radial, and j=3 is axial, $i=-\sqrt{1}$ is the imaginary unit, and $\hat{B}_{jn}$ is the n'th frequency component of the signal in the j'th channel.

As described above, the signal from the quadrupole magnet is a period n=2 signal, and therefore we can determine the orientation of the magnet relative to the sensor board by looking at the phase of $\hat{B}_{j2}$, $$\varphi_j = a\tan 2[Im(\hat{B}_{j2}), Re(\hat{B}_{j2})]/2.$$

Because the samples of sines and cosines at different frequencies are orthogonal, any disturbance to the signal that is, e.g., period n=0, 1 or 3, will be filtered out by the Fourier transform.

This relates to both external as internal disturbances. An internal component in an auto-dose pen-injector is the metal torsion spring to drive the dosing mechanism. In the case of this being magnetized, the spring field will primarily look like a period 1 signal at the sensors position. External disturbances like a dipole magnet in the vicinity of the sensors will also tend to have a signal with period 0 or 1.

Using the DFT, it is possible to filter out the disturbances from other frequencies and only determining the magnet orientation from the frequency 2 signal.

The combination of a quadrupole magnet and the DFT is therefore superior compared to a dipole magnet whose period 1 signal is similar to the frequency of common disturbances.

Using a DFT based algorithm gives a larger freedom to choose an arbitrary number of sensors, compared to a lookup based algorithm. The chosen number of sensors is preferably at least 5 due to the Nyquist sampling theorem. Besides that the number of sensors can be freely and actively used in order to filter out specific frequencies of the signal to prevent aliasing effects.

In the above disclosure the issue of both external disturbing magnet fields as well as an internal disturbing magnet field from the pen device torque spring have been addressed by the use of a quadrupole tracer magnet in combination with a sensor array comprising a number of magnetometers. In the following this issue is addressed by a different approach which may be used as an alternative or in addition to the above-described quadrupole design.

Using magnetic shields to shield magnetic systems from outside interference is commonly known and used. Normally shields are used as a barrier to either contain magnetic fields and prevent them from influencing other systems, or as a barrier to contain a system and shield it from being influenced by outside (unshielded) magnetic fields. Internal components of the system, that may introduce disturbing fields, are normally placed outside the shielded volume of the system. Indeed, it may be possible to incorporate a shield in a drug delivery device comprising a drive spring manufactured from a magnetisable material, however, as this may require a major redesign of the pen device this may not be a cost-effective option.

The technical problem to be solved, is thus to provide a magnetic shield preventing/reducing internal magnetic fields from disturbing the measurements of the magnetic sensors in a capturing device or assembly based on magnetometers. Additionally, such a shield may also serve to prevent/reduce the disturbances from "normal" external magnetic fields.

The suggested solution is to introduce a shield of mu-metal, to not only shield the sensor system from external magnetic fields, but also divert any unintended internal magnetic field introduced by the torque spring towards the shield and reduce the disturbance of the field of the tracer magnets. By reducing the strength of the disturbing field from the torque spring it may enable the use of fewer sensors and thus lower signal processing requirements to obtain required accuracy and redundancy, and thereby reduce both costs and power consumption.

Mu-metal is a nickel-iron soft magnetic alloy with very high permeability. It has several compositions, with approximately 80% nickel, 15% a few percent molybdenum and in some compositions a little copper and chromium. Mu-metal is very ductile and workable and can easily be formed into thin sheets needed for magnetic shields. However, mu-metal objects require heat treatment after they are worked into their final form.

Magnetic shields made with mu-metal works by providing a path for the magnetic lines around the shielded area instead of blocking them. The mu-metal sort of offers an "easier" path than thought the air with much lower relative permeability and thus diverts the magnetic field. However, mu-metal has a much lower saturation level and are thus not suitable for shielding against stronger magnetic fields.

Figure 8A:
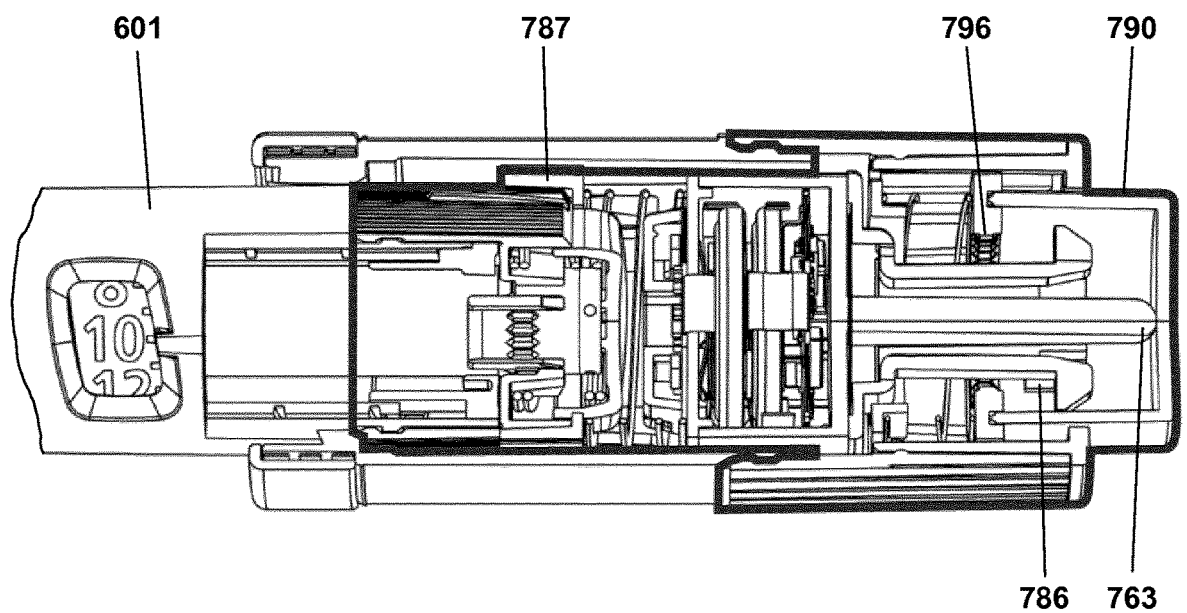
Figure 8B:
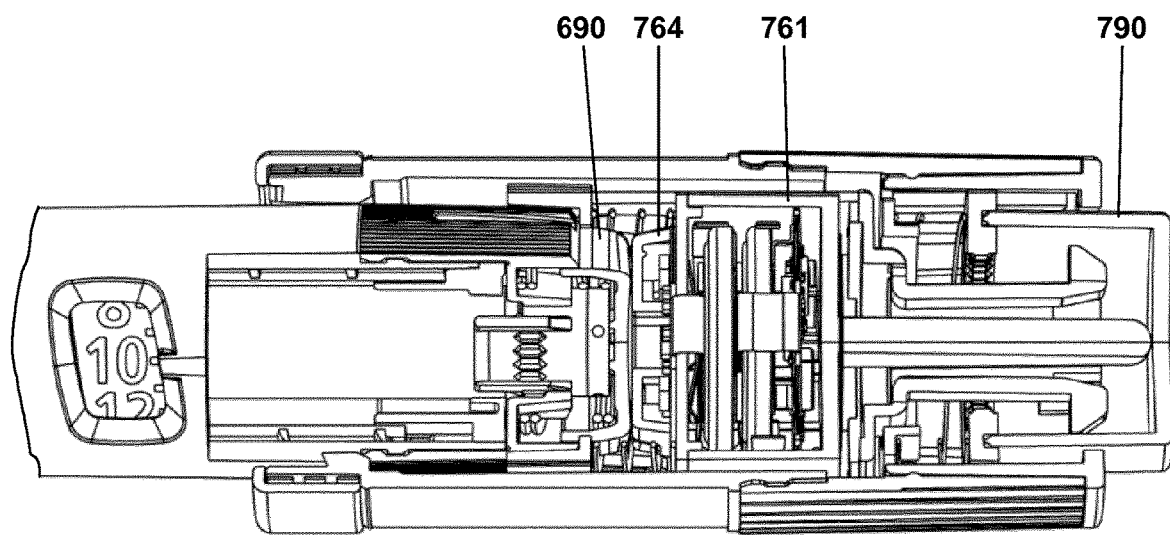
Figure 8C:
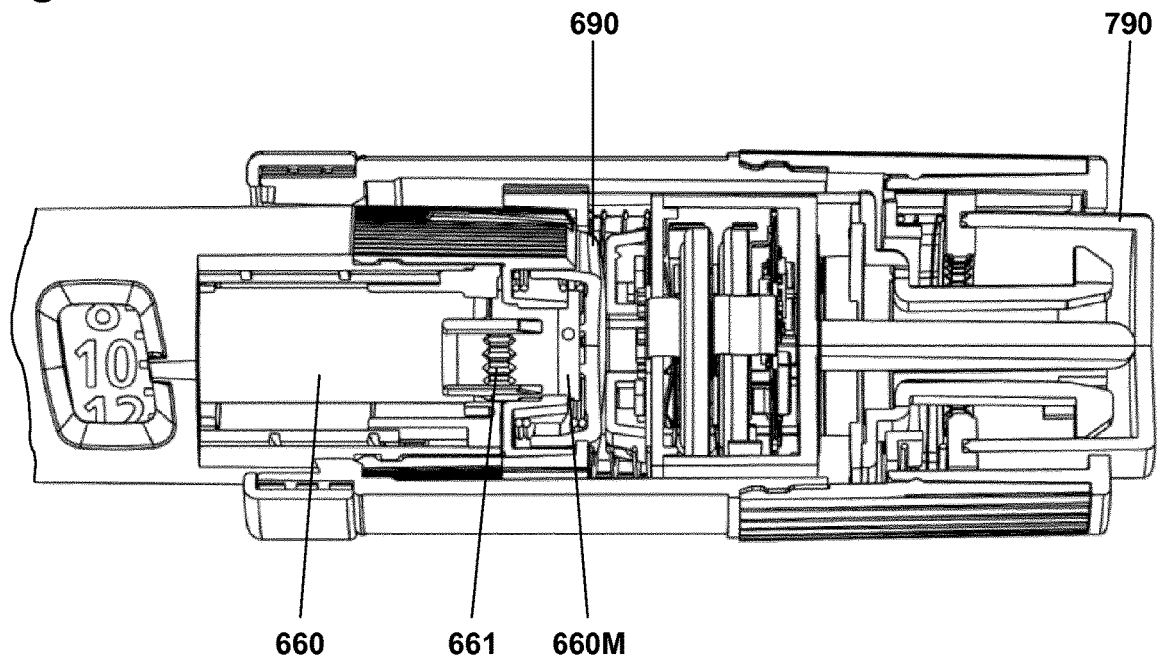
Figure 8D:
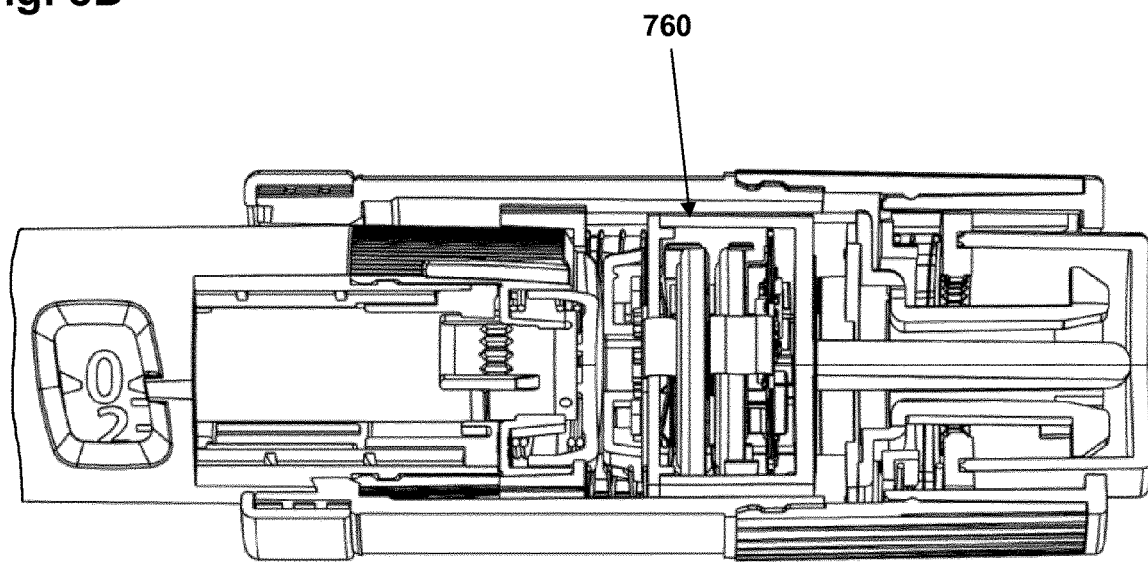
Figure 21:
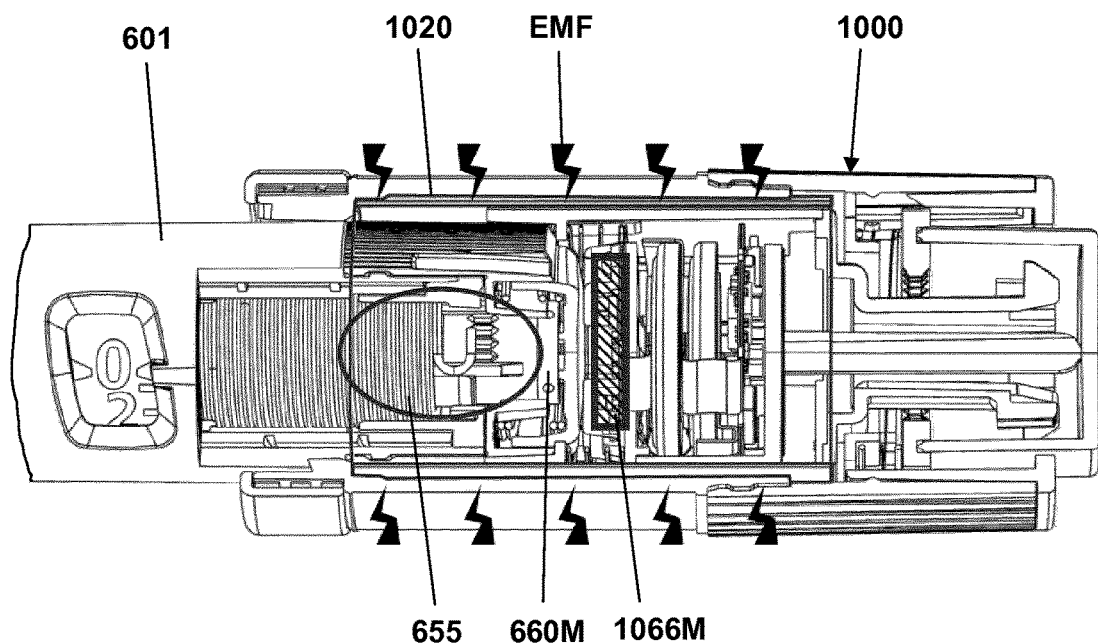
FIG. 21 shows a further embodiment of add-on device mounted on a drug delivery device.

FIG. 21 shows an assembly essentially corresponding to the assembly shown in FIG. 8A albeit with the drug delivery device torque spring 655 shown, the add-on dose logging device 1000 being provided with a cylindrical shield 1020 made of mu-metal covering the axial length of the sensors and tracer magnet volume, as well as the proximal part of the torque spring 655. The cylindrical mu-metal shield essentially absorbs the magnetic lines from a torque spring having been magnetized and guides them towards the circumferential shield and thereby limits the extent of the disturbing field of the torque spring in axial direction and thus towards the sensors. At the same time the cylindrical shield helps reduce the influence of external magnetic fields EMF on the sensor electronics arranged in the interior of the cylindrical volume.

Although the cylindrical mu-metal shield 1020 principally will also absorb magnetic lines from the tracer magnet 660M, this will influence the measuring performance to a smaller degree as (i) the torque spring 655 is axially arranged farther away from the magnetic sensors 1066M than the tracer magnet, and (ii) the torque spring is arranged radially closer to the shield than the tracer magnet. In this way the sensor system will be able to measure the magnetic field from the tracer magnet as only a smaller portion of the field is absorbed by the shield, whereas the above-described geometrical properties will allow a magnetic field from the torque spring to be absorbed by the shield to a high degree and thus influence the sensors to a smaller extent.

Figure 22:
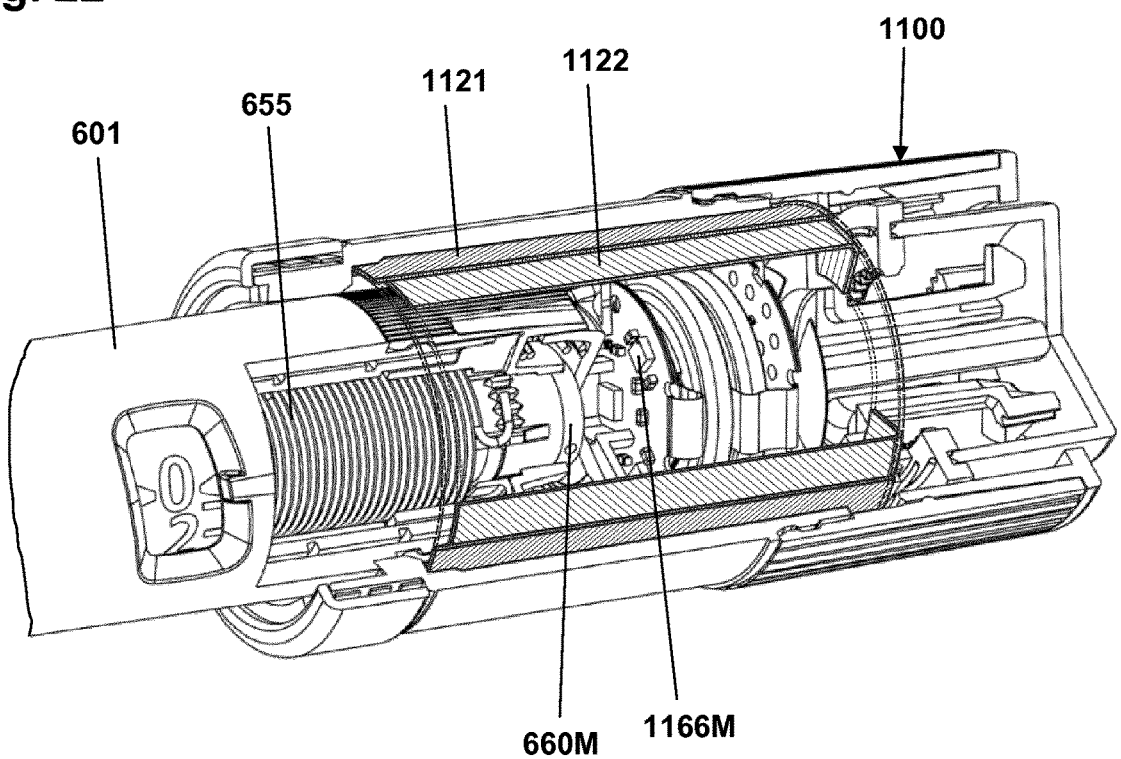
FIG. 22 shows a yet further embodiment of add-on device mounted on a drug delivery device.

FIG. 22 shows an embodiment of an add-on dose logging device 1100 in which an outer shield of steel 1121, able to handle stronger magnetic fields without saturation, is applied to provide a path for external magnetic fields. An inner shield 1122 in mu-metal is arranged to provide a path for a relative weak internal magnetic field introduced by the torque spring, without being saturated by a strong external field.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An assembly comprising a drug delivery device and an add-on device adapted to be releasably mounted on a drug delivery device, the drug delivery device comprising:
   a housing defining a reference axis,
   a drug reservoir or a structure for receiving a drug reservoir, and
   a drug expelling structure comprising a dose setting member rotatable relative to the reference axis allowing a user to set a dose amount of drug to be expelled, the dose setting member being arranged at the proximal end of the housing and comprising a generally cylindrical outer surface with at least one axially oriented drive groove,
   the add-on device comprising:
   a mounting portion with a bore adapted to receive a portion of the drug delivery device housing and the dose setting member, the mounting portion being adapted to be releasably attached to the drug delivery device housing in an axially non-moveable position,
   a drive portion adapted to be mounted in engagement with the dose setting member, the drive portion comprising at least one drive structure biased in a radially inwards direction, and
   the at least one drive structure is adapted to engage a drive groove, the at least one drive structure being biased in a radially inwards direction and being adapted to be moved radially outwards when engaging the dose setting member.

2. The add-on device as in claim 1 in combination with a drug delivery device to thereby form an assembly, the drug delivery device comprising:
   a housing defining a reference axis,
   a drug reservoir or structure for receiving a drug reservoir, and
   a drug expelling structure comprising a dose setting member rotatable relative to the reference axis allowing a user to set a dose amount of drug to be expelled, the dose setting member being arranged at the proximal end of the housing,
   whereby the drive portion can be mounted on the dose setting member in a rotationally non-engaged state with each drive structure in biased rotationally sliding engagement with the dose setting member outer surface, and
   whereby the drive portion can be rotated into a rotationally locked state on the dose setting member when the at least one drive structure is aligned with a drive groove and biased into engagement therewith.

3. The assembly as in claim 2, wherein:
   the mounting portion is adapted to be mounted rotationally locked on the drug delivery device housing, and
   the drive portion is arranged to rotate relative to the mounting portion.

4. The assembly as in claim 3, wherein the add-on device comprises an add-on dose setting member being coupled to the mounting portion rotatable free but axially locked, and which is directly or indirectly rotationally coupled to the drive portion.

5. The assembly as in claim 1, wherein:
   the mounting portion is adapted to be mounted rotationally free on the drug delivery device housing, and
   the mounting portion and the drive portion are rotationally locked to each other during dose setting.

6. The assembly as in claim 1, wherein the mounting portion and the housing comprise inter-engaging releasable coupling structure.

7. The assembly as in claim 1, wherein the mounting portion and the housing comprise inter-engaging releasable coupling structure allowing the add-on device to be mounted on the housing in one of one or more rotationally predetermined positions.

8. The assembly as in claim 1, wherein the add-on device comprises a bore adapted to axially receive a proximal portion of the drug delivery device.

9. The assembly as in claim 1, wherein the drive portion comprises a cylindrical member adapted to receive the dose setting member and being provided with at least one flexible structure forming the drive structure.

10. The assembly as in claim 9, wherein the least one flexible structure is in the form of a finger with a free end forming the drive structure.

11. The assembly as in claim 10, the drug delivery device further comprising:
    a release member actuatable between a proximal position and a distal position, the proximal position allowing a dose amount to be set, the distal position allowing the drug expelling structure to expel a set dose, the add-on device further comprising:

an add-on release member axially moveable relative to an add-on dose setting member between a dose setting state and a dose expelling state, wherein in a mounted state the add-on release member directly or indirectly engages and actuates the release member when moved distally.

12. The assembly as in claim 11, wherein:

with the add-on release member in the dose setting state the add-on dose setting member and a drive member are rotationally coupled to each other, and with the add-on release member in the dose expelling state the add-on dose setting member and the drive member have been rotationally de-coupled from each other.

13. The assembly as in claim 1, the drug delivery device further comprising:

an indicator adapted to move during expelling of a dose amount, the amount of movement being indicative of the size of the expelled dose amount, the add-on device further comprising:

a sensor structure adapted to detect the amount of rotation of the indicator during expelling of a dose amount.

14. The assembly as in claim 13, wherein the sensor structure is coupled non-rotationally to the drive portion.

15. The assembly as in claim 14, wherein:

the indicator is arranged to rotate relative to the housing and corresponding to the reference axis and comprises a plurality of dipole magnets, the sensor structure comprises:

a plurality of magnetometers arranged non-rotational relative to the housing in a mounted state and adapted to determine magnetic field values from the plurality of dipole magnets, and processor structure configured to determine on the basis of measured values from the plurality of magnetometers a rotational position and/or a rotational movement of the indicator.

16. The add-on device as in claim 1, wherein the drive portion comprises a cylindrical member adapted to receive the dose setting member and being provided with at least one flexible structure forming the drive structure.

17. The add-on device as in claim 16, wherein the least one flexible structure is in the form of a finger with a free end forming the drive structure.

18. The add-on device as in any of claim 16, the drug delivery device further comprising:

an indicator adapted to move during expelling of a dose amount, the amount of movement being indicative of the size of the expelled dose amount, the add-on device further comprising:

sensor structure adapted to detect the amount of rotation of the indicator during expelling of a dose amount.

19. The add-on device as in claim 18, wherein the sensor structure is coupled non-rotationally to the drive portion.

20. The assembly as in claim 19, wherein:

the indicator is arranged to rotate relative to the housing and corresponding to the reference axis and comprises a plurality of dipole magnets, the sensor structure comprises:

a plurality of magnetometers arranged non-rotational relative to the housing in a mounted state and adapted to determine magnetic field values from the plurality of dipole magnets, and processor structure configured to determine on the basis of measured values from the plurality of magnetometers a rotational position and/or a rotational movement of the indicator.

* * * * *

UNITED STATES PATENT AND TRADEMARK OFFICE
CERTIFICATE OF CORRECTION

PATENT NO. : 11,759,574 B2
APPLICATION NO. : 16/969207
DATED : September 19, 2023
INVENTOR(S) : Bennie Peder Smiszek Pedersen et al.

It is certified that error appears in the above-identified patent and that said Letters Patent is hereby corrected as shown below:

In the Claims

At Column 31, Claim number 1, Line number 49, please delete as follows: "assembly comprising a drug delivery device and an"

At Column 32, Claim number 5, Line number 41, please delete "assembly" and replace with "add-on device"

At Column 32, Claim number 6, Line number 46, please delete "assembly" and replace with "add-on device"

At Column 32, Claim number 7, Line number 49, please delete "assembly" and replace with "add-on device"

At Column 32, Claim number 8, Line number 54, please delete "assembly" and replace with "add-on device"

At Column 32, Claim number 9, Line number 57, please delete "assembly" and replace with "add-on device"

At Column 32, Claim number 10, Line number 61, please delete "assembly" and replace with "add-on device"

At Column 32, Claim number 11, Line number 64, please delete "assembly" and replace with "add-on device"

At Column 33, Claim number 12, Line number 10, please delete "assembly" and replace with "add-on device"

Signed and Sealed this
Twenty-seventh Day of August, 2024

Katherine Kelly Vidal
*Director of the United States Patent and Trademark Office*

At Column 33, Claim number 13, Line number 18, please delete "assembly" and replace with "add-on device"

At Column 33, Claim number 14, Line number 26, please delete "assembly" and replace with "add-on device"

At Column 33, Claim number 15, Line number 28, please delete "assembly" and replace with "add-on device"